US012245843B2

United States Patent
An et al.

(10) Patent No.: US 12,245,843 B2
(45) Date of Patent: Mar. 11, 2025

(54) DISPLAY DEVICE WITH INTERGRATED BIOMETRIC MEASUREMENT AND REAL-TIME ADAPTIVE LIGHT SENSING

(71) Applicant: SAMSUNG DISPLAY CO., LTD., Yongin-si (KR)

(72) Inventors: Jong Yeop An, Yongin-si (KR); Chul Kim, Yongin-si (KR); Gyeong Ub Moon, Yongin-si (KR); Dong Wook Yang, Yongin-si (KR); Hyeon Jun Lee, Yongin-si (KR)

(73) Assignee: SAMSUNG DISPLAY CO., LTD., Yongin-si (KR)

( * ) Notice: Subject to any disclaimer, the term of this patent is extended or adjusted under 35 U.S.C. 154(b) by 0 days.

(21) Appl. No.: 18/389,238

(22) Filed: Nov. 14, 2023

(65) Prior Publication Data

US 2024/0341606 A1 Oct. 17, 2024

(30) Foreign Application Priority Data

Apr. 11, 2023 (KR) ........................ 10-2023-0047840

(51) Int. Cl.
*G06F 3/041* (2006.01)
*A61B 5/021* (2006.01)
(Continued)

(52) U.S. Cl.
CPC ...... *A61B 5/02141* (2013.01); *A61B 5/02433* (2013.01); *G06F 3/0416* (2013.01);
(Continued)

(58) Field of Classification Search
CPC ............ A61B 5/02141; A61B 5/02433; A61B 5/6898; G06F 3/0446; G06F 3/0416;
(Continued)

(56) References Cited

U.S. PATENT DOCUMENTS

2006/0244693 A1* 11/2006 Yamaguchi ............ H10K 59/60
345/76
2019/0013368 A1* 1/2019 Chung ................... H10K 59/40
(Continued)

FOREIGN PATENT DOCUMENTS

KR  10-2020-0007312  1/2020
KR  10-2021-0014559  2/2021
KR  10-2023-0151587  11/2023

OTHER PUBLICATIONS

F. Elsamna, et al., "Comparative Design Study for Power Reduction in Organic Optoelectronic Pulse Meter Sensor", Biosensors 2019, 9, 48, pp. 2-13.

*Primary Examiner* — Richard J Hong
(74) *Attorney, Agent, or Firm* — F. CHAU & ASSOCIATES, LLC

(57) ABSTRACT

A display device for measuring biometric information such as blood pressure by utilizing both display pixels and light sensing pixels within a display panel. The display device includes a main driving circuit that dynamically sets and adjusts light emission conditions, including emission color and luminance based on the user's touch area and shape, thereby optimizing the detection of biosignals such as pulse waves. The system enhances the signal-to-noise ratio (SNR) and improves the accuracy of biometric measurements.

18 Claims, 20 Drawing Sheets

(51) Int. Cl.
    *A61B 5/024* (2006.01)
    *G06F 3/044* (2006.01)
    *G09G 3/3233* (2016.01)

(52) U.S. Cl.
    CPC ......... *G06F 3/0446* (2019.05); *G09G 3/3233* (2013.01); *G06F 2203/04105* (2013.01); *G09G 2300/0842* (2013.01); *G09G 2354/00* (2013.01); *G09G 2360/14* (2013.01); *G09G 2380/08* (2013.01)

(58) Field of Classification Search
    CPC ........ G06F 2203/04105; G09G 3/3233; G09G 2300/0842; G09G 2354/00; G09G 2360/14; G09G 2380/08; H10K 59/131; H10K 59/65; H10K 59/805; H10K 59/12; H10K 59/40; H10K 59/60; H01L 29/66477; G06V 40/1306; G06V 30/333
    See application file for complete search history.

(56) References Cited

U.S. PATENT DOCUMENTS

| | | | |
|---|---|---|---|
| 2019/0114458 A1* | 4/2019 | Cho | G06V 40/1306 |
| 2020/0111851 A1* | 4/2020 | Park | H10K 59/12 |
| 2021/0036046 A1* | 2/2021 | Kwon | G06V 30/333 |
| 2021/0067618 A1* | 3/2021 | Hong | A61B 5/6898 |
| 2021/0257420 A1* | 8/2021 | Park | H10K 59/805 |
| 2024/0138169 A1* | 4/2024 | Kusunoki | H10K 59/131 |
| 2024/0164166 A1* | 5/2024 | Kubota | H01L 29/66477 |
| 2024/0196675 A1* | 6/2024 | Kimura | H10K 59/65 |

* cited by examiner

DISPLAY DEVICE WITH INTERGRATED BIOMETRIC MEASUREMENT AND REAL-TIME ADAPTIVE LIGHT SENSING

CROSS-REFERENCE TO RELATED APPLICATION

This application claims priority under 35 U.S.C. § 119 to Korean Patent Application No. 10-2023-0047840, filed on Apr. 11, 2023, in the Korean Intellectual Property Office, the disclosure of which is incorporated by reference herein in its entirety.

1. Technical Field

The present disclosure relates to a display device.

2. Description of the Related Art

As society becomes increasingly information-oriented, the demand for display devices continues to grow. These devices are now integral to a variety of electronic devices, including smart phones, digital cameras, laptop computers, tablets, navigation devices, and smart televisions. Portable display devices like smartphones and tablets often come equipped with a variety of features including image capture, fingerprint recognition, facial recognition, etc.

Recently, in the healthcare industry, there is a push to develop move convenient methods for acquiring biometric information. For example, there is an effort to adapt traditional oscillometric blood pressure measurement devices into portable blood pressure measurement devices. However, a portable blood pressure measurement device requires its own light source, sensor and display. Thus, carrying it along with a smart phone or tablet can be cumbersome for users.

Recently, efforts have been made to integrate portable display devices such as smart phones and tablets with portable blood pressure measurement devices. However, challenges arise due to factors like the display device's luminance, the lifespan and reliability of its light source, and others. These factors make it tough to achieve optimal conditions for measuring biometric information such as Signal-to-Noise Ratio (SNR).

SUMMARY

Embodiments of the present disclosure provide a display device capable of detecting a photoplethysmography signal using an image display panel and measuring biometric information such as a user's blood pressure.

Embodiments of the present disclosure also provide a display device capable of increasing Signal-to-Noise Ratio (SNR) and biometric information measurement accuracy by setting and correcting light sensing conditions used to detect biosignals such as pulse wave signals in real time according to the touch shape and touch area of a user's body part.

According to an embodiment of the present disclosure, there is provided a display device including: display pixels arranged in a display area of a display panel; light sensing pixels arranged in the display area; a display scan driver configured to cause the display pixels to emit light; a light sensing scan driver configured to cause the light sensing pixels to sense light; and a main driving circuit configured to measure a user's biometric information by using light sensing signals provided from the light sensing pixels, wherein the main driving circuit senses the user's touch area when the user's biometric information is measured, and sets a biometric information measurement area and a measurement condition, which includes an emission color and an emission luminance, according to a shape of a sensed touch area and touch area information to measure the user's biometric information.

According to an embodiment of the present disclosure, there is provided a display device including: display pixels arranged in a display area of a display panel; light sensing pixels arranged in the display area; infrared light emitting pixels arranged in the display area; a display scan driver driven so that the display pixels emit light; a light sensing scan driver driven so that the light sensing pixels sense light; a touch sensing unit disposed on a front surface of the display panel and configured to sense a user's touch and output a touch sensing signal, a touch driving circuit configured to generate touch data and touch coordinate data according to a magnitude change and an output position of the touch sensing signal; and a main driving circuit configured to measure the user's biometric information by using light sensing signals received through the light sensing pixels, wherein the main driving circuit senses the user's touch area when the biometric information is measured, and sets a biometric information measurement area and a measurement condition that includes an emission color and an emission luminance according to a shape of a sensed touch area and touch area information to measure the user's biometric information.

According to embodiments of the present disclosure, when light output from an image display pixel is reflected from a part of the body such as a user's finger, the reflected light is sensed by a light sensing pixel of the display panel, to detect biometric information such as the user's blood pressure. This way, biometric information such as the user's blood pressure can be detected using the display panel of the display device.

According to the embodiments of the present disclosure, biometric information can be measured by setting and correcting light sensing conditions for detecting biosignals such as pulse wave signals in real time according to the touch shape and touch area of a user's body part. Accordingly, the SNR for biometric information measurement can be increased and the user's biometric information can be more accurately measured according to the characteristics of the user's body part, such as the face, scalp, and finger blood vessels.

BRIEF DESCRIPTION OF THE DRAWINGS

The above and other features of the present disclosure will become more apparent by describing in detail embodiments thereof with reference to the attached drawings, in which.

DETAILED DESCRIPTION OF THE EMBODIMENTS

The present disclosure will now be described more fully hereinafter with reference to the accompanying drawings, in which embodiments of the disclosure are shown. This disclosure may, however, be embodied in different forms and should not be construed as limited to the embodiments set forth herein.

It will also be understood that when a layer is referred to as being "on" another layer or substrate, it can be directly on the other layer or substrate, or intervening layers may also be present. The same reference numbers may indicate the same components throughout the specification.

It will be understood that, although the terms "first," "second," etc. may be used herein to describe various elements, these elements should not be limited by these terms. These terms are used to distinguish one element from another element. For instance, a first element discussed below could be termed a second element. Similarly, the second element could also be termed the first element.

Each of the features of the various embodiments of the present disclosure may be combined, in part or in whole, and technically various interlocking and driving are possible. Each embodiment may be implemented independently of each other or may be implemented together in an association.

Hereinafter, specific embodiments will be described with reference to the accompanying drawings.

Figure 1:
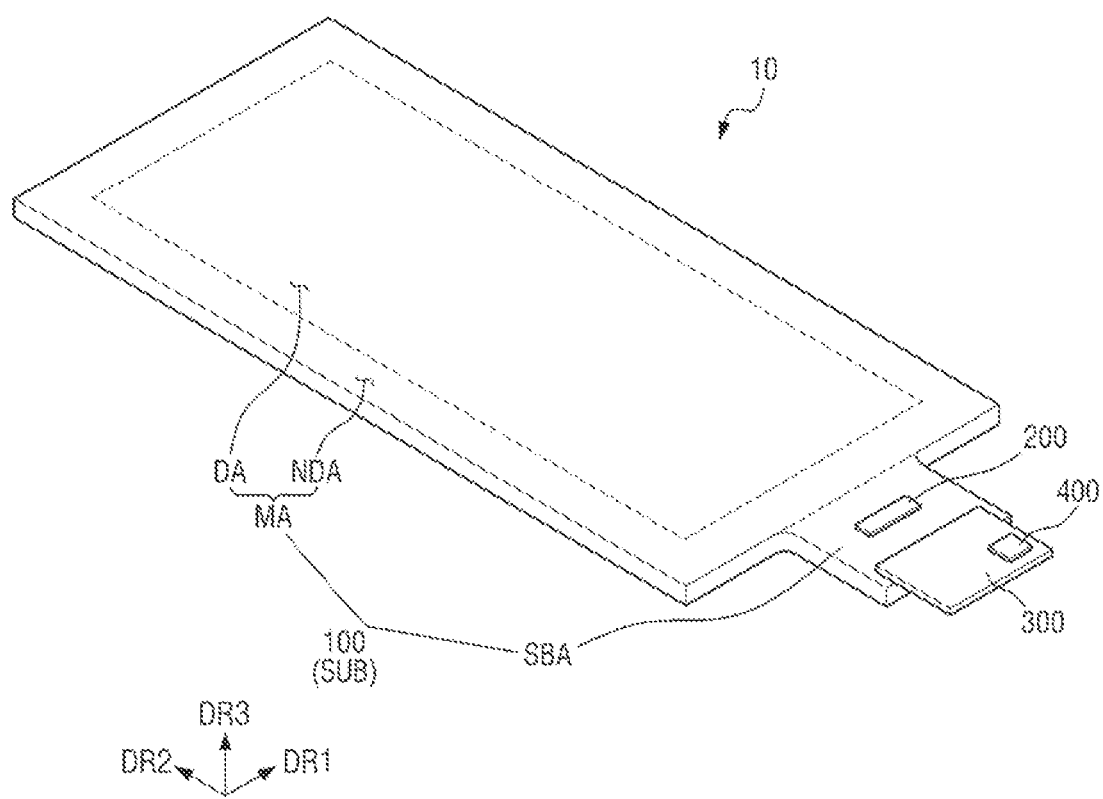
FIG. 1 is a perspective view of a display device according to an embodiment of the present disclosure.
Figure 2:
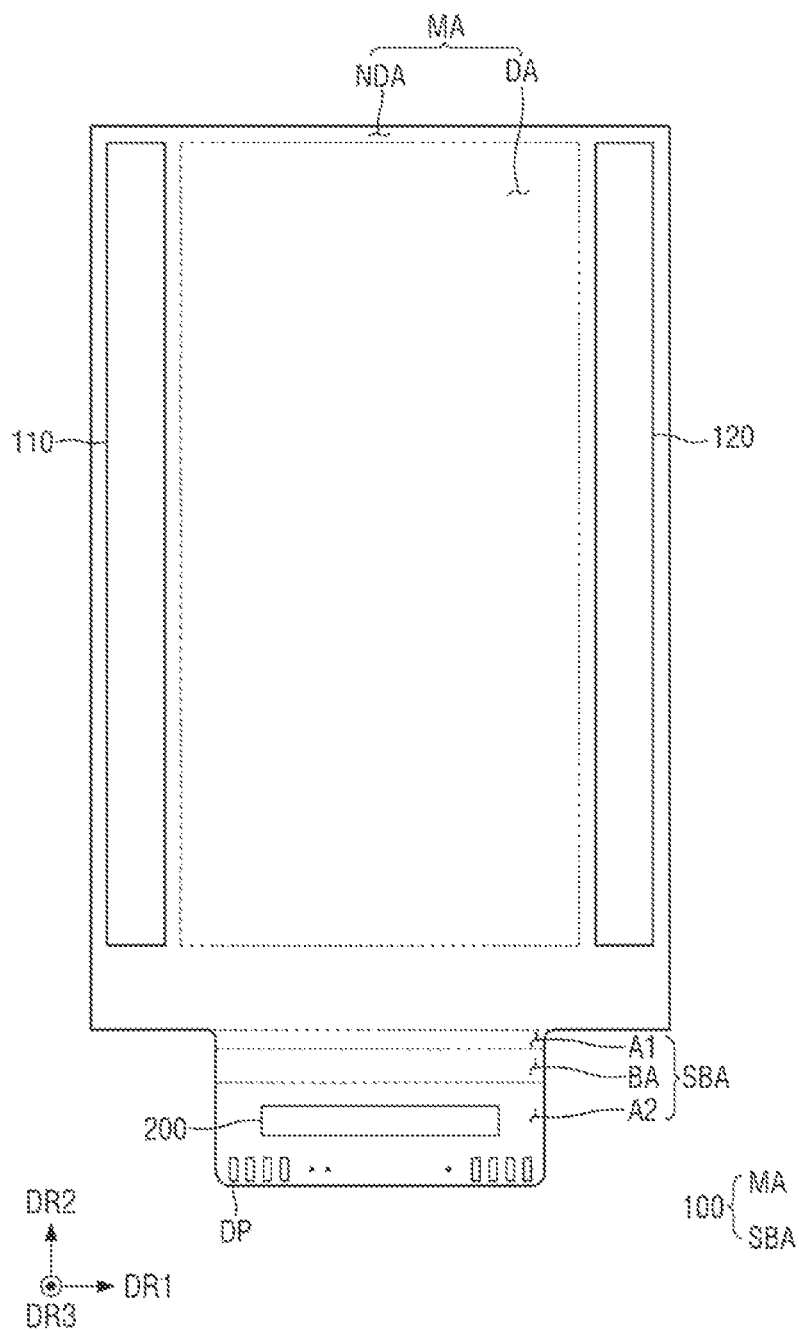
FIG. 2 is a plan view showing the arrangement structure of a display panel and a display driving circuit shown in FIG. 1.
Figure 3:
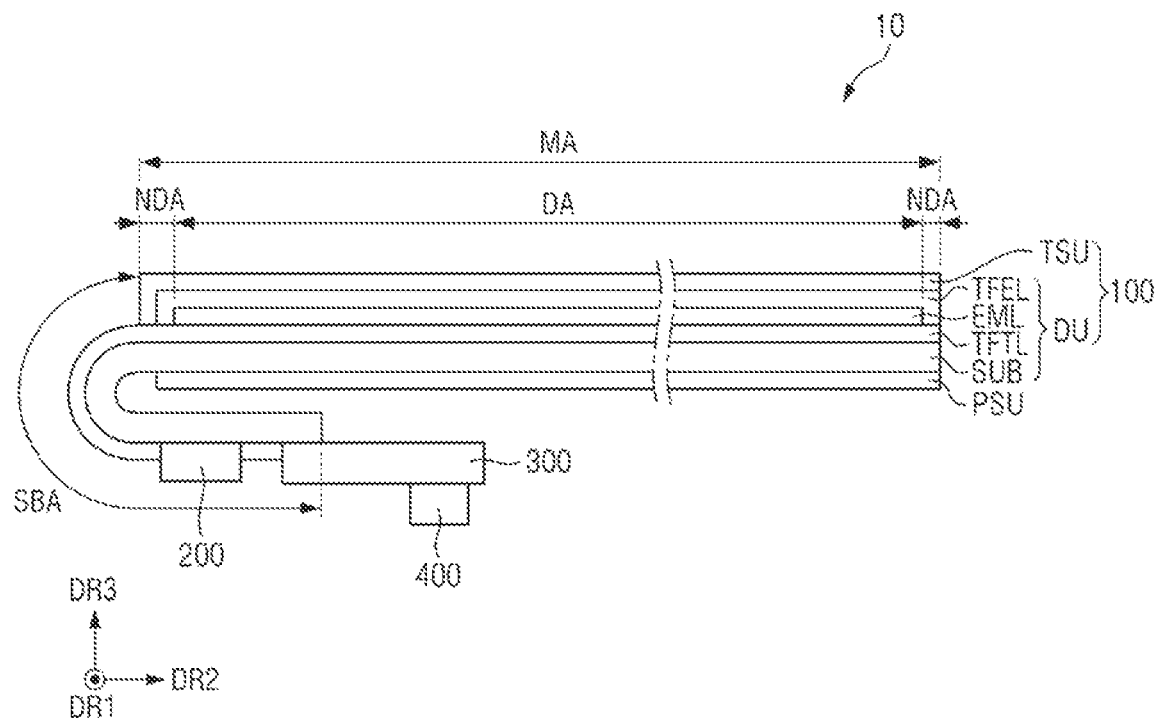
FIG. 3 is a side view showing the configuration of the display device shown in FIG. 1.

FIG. 1 is a perspective view of a display device according to an embodiment of the present disclosure. FIG. 2 is a plan view showing the arrangement structure of a display panel and a display driving circuit shown in FIG. 1. FIG. 3 is a side view showing the configuration of the display device shown in FIG. 1.

First, referring to FIGS. 1 and 2, a display device 10 according to an embodiment may be applied to portable electronic devices such as mobile phones, smartphones, tablet personal computers (PCs), mobile communication terminals, electronic notebooks, electronic books, portable multimedia players (PMPs), navigation devices, and ultra mobile PCs (UMPCs). Alternatively, the display device 10 according to an embodiment may be applied as a display unit of televisions, laptop computers, monitors, billboards, or the Internet of Things (IOTs). Alternatively, the display device 10 according to an embodiment may be applied to wearable devices such as smart watches, watch phones, glasses-type displays, and head mounted displays (HMDs). Alternatively, the display device 10 according to an embodiment may be applied to a center information display (CID) disposed on an instrument board, a center fascia, or a dashboard of a vehicle, a room mirror display substituting for a side mirror of the vehicle, or a display disposed on a rear surface of a front seat as an entertainment device for a rear seat passenger of the vehicle.

The display device 10 may be a light emitting display device such as an organic light emitting display device using an organic light emitting diode (LED), a quantum dot light emitting display device including a quantum dot light emitting layer, an inorganic light emitting display device including an inorganic semiconductor, and a micro light emitting display device using a micro LED or nano LED. Hereinafter, it has been mainly described that the display device 10 is the organic light emitting display device, but the present disclosure is not limited thereto.

Referring to FIGS. 1 and 3, the display device 10 includes a display panel 100, a main driving circuit 200, a touch sensing unit TSU, a pressure sensing unit PSU, a circuit board 300, and a touch driving circuit 400.

The display panel 100 may have a rectangular shape, in a plan view, having short sides in a first direction DR1 and long sides in a second direction DR2 crossing the first direction DR1. A corner where the short side in the first direction DR1 and the long side in the second direction DR2 meet may be right-angled or rounded with a predetermined curvature. The shape of the display panel 100 in a plan view is not limited to the rectangular shape, and may be other polygonal shapes, such as a circular shape, or an elliptical shape. The display panel 100 may be flat, but is not limited thereto. For example, the display panel 100 may include curved surface parts formed at left and right ends thereof, wherein the curved surface parts have a constant curvature or a variable curvature. In addition, the display panel 100 may be flexible such that it can be curved, bent, folded, or rolled.

A substrate SUB of the display panel 100 may include a main area MA and a sub-area SBA.

The main area MA may include a display area DA for displaying an image and a non-display area NDA, which is a peripheral area of the display area DA.

The non-display area NDA may neighbor the display area DA. The non-display area NDA may be an area outside the display area DA. The non-display area NDA may surround the display area DA. The non-display area NDA may be an edge area of the display panel 100.

The display area DA includes display pixels that display images, and light sensing pixels that sense light reflected off a part of a user's body, such as a finger or face. In addition, the display area DA may further include infrared light emitting pixels that emit infrared light.

The display area DA may occupy most of the main area MA. The display area DA may be disposed at the center of the main area MA.

The display area DA may be divided into an image display area in which only display pixels are disposed without light sensing pixels, and a biometric information measurement area in which light sensing pixels, infrared light emitting pixels, and display pixels are disposed. For example, a first area of the display area DA may include only display pixels and a second area of the display DA may include light sensing pixels, infrared light emitting pixels, and display pixels. In other words, the light sensing pixels may be disposed together with the display pixels only in a predetermined portion of the display area DA of the display panel 100, e.g., only in a biometric information measurement area. In the following description, it is assumed that the display pixels, the infrared light emitting pixels, and the light sensing pixels are alternately arranged in the display area DA.

Referring to FIGS. 2 and 3, the sub-area SBA may protrude from one side of the main area MA in the second direction DR2. The length of the sub-area SBA in the second direction DR2 may be smaller than the length of the main area MA in the second direction DR2. The length of the sub-area SBA in the first direction DR1 may be substantially less than the length of the main area MA in the first direction DR1 or may be substantially equal to the length of the main area MA in the first direction DR1.

The sub-area SBA may include a first area A1, a second area A2 and a bending area BA.

The first area A1 protrudes from one side of the main area MA in the second direction DR2. A first side of the first area A1 may be in contact with the non-display area NDA of the main area MA, and a second side of the first area A1 opposite the first side of the first area A1 may be in contact with the bending area BA.

In the second area A2, pads DP and the main driving circuit 200 are disposed. The main driving circuit 200 may be attached to driving pads of the second area A2 using a conductive adhesive member such as an anisotropic conductive layer. The circuit board 300 may be attached to the pads DP of the second area A2 using a conductive adhesive member. A first side of the second area A2 may be in contact with the bending area BA.

The bending area BA is a part of the display panel 100 that is bendable. When the bending area BA is bent, the second area A2 may be disposed under the first area A1 and under the main area MA. The bending area BA may be disposed between the first area A1 and the second area A2. A first side of the bending area BA may be in contact with the first area A1, and a second side of the bending area BA opposite the first side of the bending area BA may be in contact with the second area A2.

As shown in FIG. 3, the sub-area SBA may be bent so that it is located under the main area MA. The sub-area SBA may overlap with the main area MA in a third direction DR3.

A touch sensing unit TSU for sensing a body part such as a finger and an electronic pen is formed or disposed on the front portion of the display panel 100. The touch sensing unit TSU may include a plurality of touch electrodes to sense a user's touch by capacitive sensing.

The touch sensing unit TSU includes a plurality of touch electrodes arranged such that they cross each other in the first and second directions DR1 and DR2. For example, the plurality of touch electrodes includes a plurality of driving electrodes arranged in parallel and spaced apart from one another in the first direction DR1, and a plurality of sensing electrodes arranged in parallel and spaced apart from one another in the second direction DR2, the sensing electrodes crossing the driving electrodes with an organic material layer or an inorganic material layer therebetween. The driving electrodes and the sensing electrodes may be extended in a wiring area between the display pixels and the light sensing pixels so that they do not overlap with the display pixels or the light sensing pixels arranged in the display area DA. Such driving electrodes and sensing electrodes form mutual capacitance, and transmit touch sensing signals that are changed according to a user's touch to the touch driving circuit 400.

The touch driving circuit 400 supplies touch driving signals to the plurality of driving electrodes, and receives touch sensing signals from the plurality of sensing electrodes. The touch driving circuit 400 senses a change in mutual capacitance between the driving electrodes and the sensing electrodes based on a change in the magnitude of the touch sensing signals. The touch driving circuit 400 generates touch data according to a change in mutual capacitance between driving electrodes and sensing electrodes and derives a sensed touch position. Accordingly, coordinate data of the touch-sensed position may be supplied to the main driving circuit 200.

The pressure sensing unit PSU which detects pressure applied by a body part such as a finger may be disposed or formed on the rear surface of the display panel 100, for example, on the rear surface of the substrate SUB. The pressure sensing unit PSU may be formed as a transparent sheet in which a plurality of transparent electrodes are arranged in vertical and horizontal directions, and may be disposed on the front surface of the main area MA. Alternatively, the pressure sensing unit PSU may be disposed or formed inside or on the front surface portion of the display panel 100.

For example, the pressure sensing unit PSU includes a plurality of pressure sensing electrodes arranged such that they cross each other in the first and second directions DR1 and DR2. The plurality of pressure sensing electrodes includes a plurality of lower electrodes arranged in parallel and spaced apart from one another in the first direction DR1, and a plurality of upper electrodes arranged in parallel and spaced apart from one another in the second direction DR2, wherein the upper electrodes cross the lower electrodes with a transparent inorganic (or organic) material layer therebetween. Such lower electrodes and upper electrodes form mutual capacitance with a transparent inorganic (or organic) material layer therebetween, and transmit pressure sensing signals that are changed according to a user's touch pressure to the touch driving circuit 400.

Figure 4:
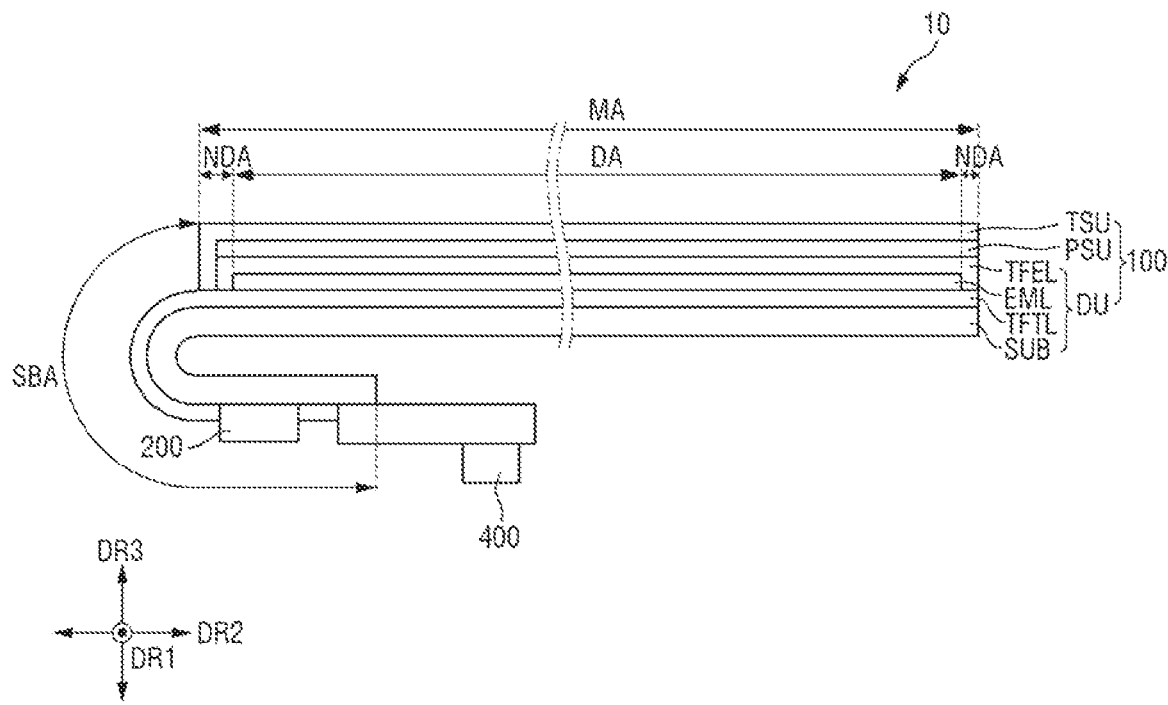
FIG. 4 is another side view showing the configuration of the display device shown in FIG. 1.

FIG. 4 is another side view showing the configuration of the display device shown in FIG.

FIG. 4 illustrates an example in which the pressure sensing unit PSU is disposed on the front surface of the display panel 100, for example, on a surface between the display panel 100 and the touch sensing unit TSU.

When the pressure sensing unit PSU is disposed on the front surface of the display panel 100, the pressure sensing electrodes of the pressure sensing unit PSU, in other words, the plurality of lower electrodes and upper electrodes may be formed to extend in a wiring area between the display pixels and the light sensing pixels so as not to overlap with each of the display pixels and the light sensing pixels arranged in the display area DA. The touch driving circuit 400 may supply a reference voltage to the lower electrodes of the pressure sensing unit PSU, receive pressure sensing signals from the upper electrodes of the pressure sensing unit PSU, and detect a self-capacitance change in areas that are pressed through the pressure sensing signals. Accordingly, the touch driving circuit 400 may generate pressure data according to the amount of change in self-capacitance and sensing coordinate data corresponding to the pressure-sensed position, and supply the generated data (e.g., pressure data and sensing coordinate data) to the main driving circuit 200. The pressure sensing unit PSU may be applied in a variety of other structures besides the structure using the pressure sensing electrodes, and is not limited to the description of FIGS. 3 and 4.

The circuit board 300 may be attached to one end of the sub-area SBA. Accordingly, the circuit board 300 may be electrically connected to the display panel 100 and the main driving circuit 200. The display panel 100 and the main driving circuit 200 may receive digital video data, timing signals, and driving voltages through the circuit board 300. The circuit board 300 may be a flexible printed circuit board, a printed circuit board, or a flexible film such as a chip on film.

The main driving circuit 200 may generate electrical signals such as data voltages and control signals and for driving the display panel 100. Each of the touch driving circuits 400, including the main driving circuit 200, may be attached to display a panel or the circuit board 300 by an integrated circuit (IC) and is formed using a chip on glass (COG) method, a chip on plastic (COP) method, or an ultrasonic bonding method, but the present disclosure is not limited thereto. For example, the touch driving circuit 400 including the main driving circuit 200 may be attached on the circuit board 300 in a chip on film (COF) method.

Figure 5:
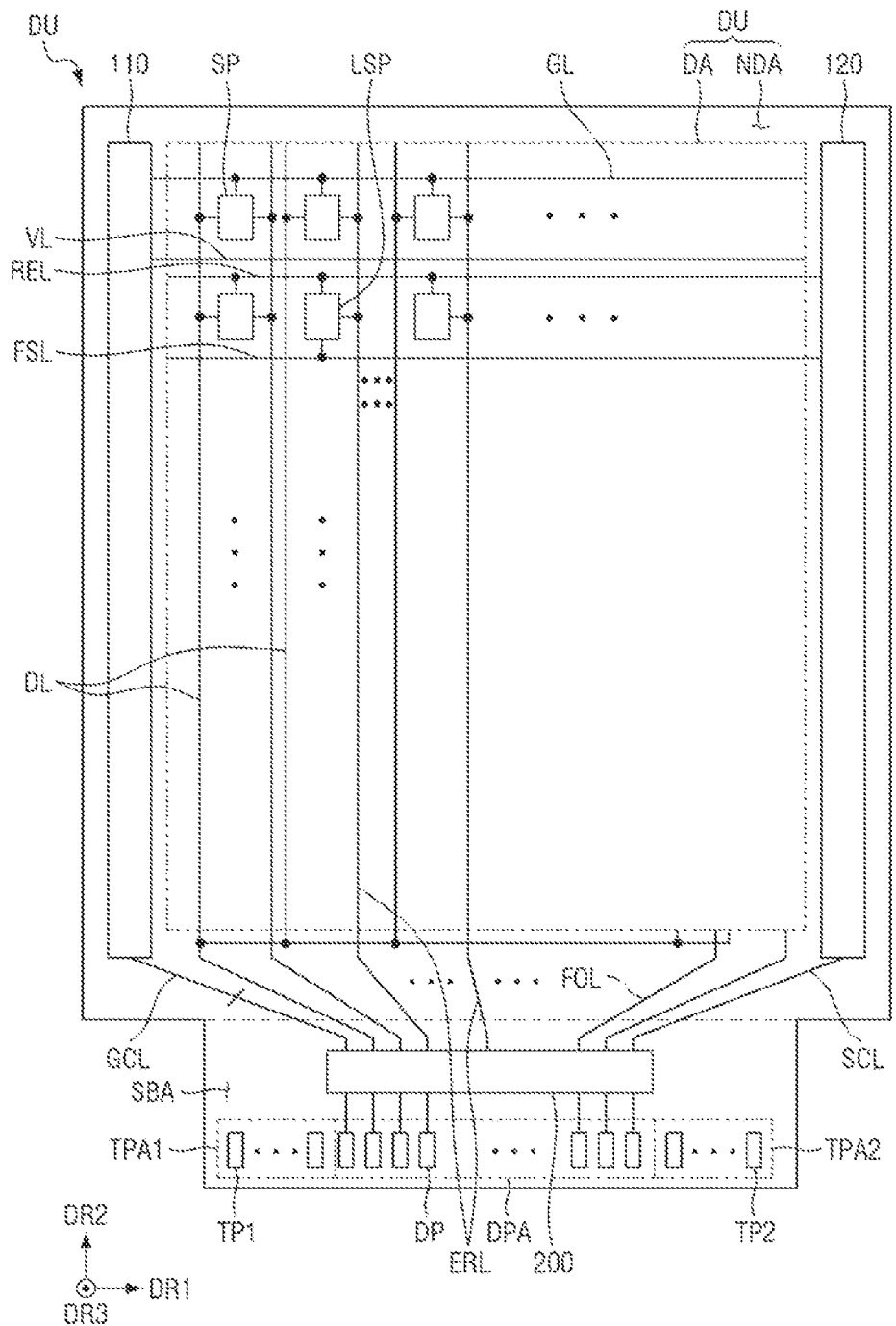
FIG. 5 is a schematic layout diagram illustrating an example of a display panel illustrated in FIGS. 1 to 4.

FIG. 5 is a schematic layout diagram illustrating an example of the display panel illustrated in FIGS. 1 to 4. For example, FIG. 5 is a layout diagram illustrating a display area DA and a non-display area NDA of a display module DU in a state before the touch sensing unit TSU is formed. FIG. 3 further shows that the display module DU includes a thin film transistor layer TFTL, an emission layer EML and an encapsulation layer TFEL.

Referring to FIG. 5 together with FIGS. 3 and 4, a display scan driver 110, a light sensing scan driver 120, and the main driving circuit 200 may be disposed in the display panel 100 of the display device 10 according to an embodiment. In addition, the touch driving circuit 400, a power supply unit, and the like, may be disposed on the circuit board 300 connected to the display panel 100. Here, both the main driving circuit 200 and the touch driving circuit 400 may be integrally formed as a single-chip and may be mounted on the display panel 100 or the circuit board 300. However, for convenience of functional explanation, an example in which the main driving circuit 200 and the touch driving circuit 400 are formed as different integrated circuits, respectively, will hereinafter be described.

Referring to FIG. 5, the display panel 100 may include display pixels SP, infrared light emitting pixels, light sensing pixels LSP, display scan lines GL, emission control lines VL, data lines DL, light sensing scan lines FSL, sensing reset lines REL, and light sensing lines ERL that are disposed in the display area DA. Each of the display scan driver 110 and the light sensing scan driver 120 is disposed in the non-display area NDA.

The display scan lines GL sequentially supply display scan signals applied in units of each horizontal line from the display scan driver 110 to each of the display pixels SP, the light sensing pixels LSP, and the infrared light emitting pixels for each horizontal line. The display scan lines GL may extend in the first direction DR1 and may be spaced apart from each other in the second direction DR2 crossing the first direction DR1.

The emission control lines VL sequentially supply emission control signals applied in units of each horizontal line from the display scan driver 110 to the display pixels SP, the light sensing pixels LSP, and the infrared light emitting pixels for each horizontal line. The emission control lines VL may extend in the first direction DR1 in parallel with the display scan lines GL and may be spaced apart from each other in the second direction DR2 crossing the first direction DR1.

The data lines DL may supply data voltages received from the main driving circuit 200 to the plurality of display pixels SP. The plurality of data lines DL may extend in the second direction DR2 and may be spaced apart from each other in the first direction DR1.

The light sensing scan lines FSL sequentially supply sensing scan signals applied in units of each horizontal line from the light sensing scan driver 120 to a plurality of light sensing pixels LSP. The light sensing scan lines FSL may extend in the first direction DR1 and may be spaced apart from each other in the second direction DR2 crossing the first direction DR1.

The sensing reset lines REL sequentially supply sensing reset signals applied in units of each horizontal line from the light sensing scan driver 120 to the plurality of light sensing pixels LSP for each horizontal line. The sensing reset lines REL may extend in the first direction DR1 in parallel with the light sensing scan lines FSL and may be spaced apart from each other in the second direction DR2 crossing the first direction DR1.

The light sensing lines ERL are connected between the respective light sensing pixels LSP and the main driving circuit 200 to supply light sensing signals output from the respective light sensing pixels LSP to the main driving circuit 200. The light sensing lines ERL may be disposed and extended in the second direction DR2 according to a direction in which the main driving circuit 200 is disposed and may be spaced apart from each other in the first direction DR1.

The non-display area NDA may surround the display area DA. The non-display area NDA may include the display scan driver 110, the light sensing scan driver 120, fan-out lines FOL, gate control lines GCL, and light sensing control lines SCL.

The display pixels SP and the light sensing pixels LSP may each form a first unit pixel and be arranged in a matrix form in the first direction DR1 and the second direction DR2 in the display area DA. In addition, each of the display pixels SP and the infrared light emitting pixels may constitute a second unit pixel, and each second unit pixel may alternate with each first unit pixel to form a matrix in the display area DA.

For example, three display pixels SP each displaying red, green, and blue light and one light sensing pixel LSP may form one first unit pixel. In addition, three display pixels SP each displaying red, green, and blue light and one infrared light emitting pixel ISP may form one second unit pixel. The first unit pixels and the second unit pixels may alternate in a horizontal or vertical stripe form to be arranged in a matrix form. Alternatively, the first unit pixels and the second unit pixels may be alternately arranged in a zigzag pattern on a plane and may be arranged in a matrix form in one diagonal direction.

Each of the red, green, and blue display pixels SP and the infrared light emitting pixels may be connected to one of the display scan lines GL and one of the emission control lines VL. During the image display period, the red, green, and blue display pixels SP may be supplied with a data voltage of the data line DL according to the display scan signal of the display scan line GL and the emission control signal of the emission control line VL, and may supply a driving current to a light emitting element according to the data voltage to emit light. Here, during a period for measuring the biometric information such as blood pressure, the display pixels SP displaying at least one color among the red, green, and blue may selectively receive the data voltage for light emission together with the display scan signal and light emission control signal to emit light. In other words, during a biometric information acquisition period, the display pixels SP may receive the data voltage and the light emission control signal. In addition, during the period for measuring biometric information such as blood pressure, the infrared light emitting pixels may selectively receive a data voltage for light emission together with the display scan signal and the light emission control signal to emit light. In other words, during the biometric acquisition period, the infrared light emitting pixels may receive the data voltage, the display scan signal and the light emission control signal.

The light sensing pixels LSP may be arranged alternately with the red, green, and blue display pixels SP in a vertical or horizontal direction. Each of the light sensing pixels LSP may be connected to one of the light sensing scan lines FSL, one of the sensing reset lines REL, and one of the light sensing lines ERL. During the period for measuring biometric information such as blood pressure, the respective light sensing pixels LSP may be reset in response to the sensing reset signals from the sensing reset lines REL, and may generate light sensing signals corresponding to an amount of reflected light incident from a front direction. In addition, the respective light sensing pixels LSP may transmit the light sensing signals to the light sensing lines ERL in response to the sensing scan signals from the light sensing scan lines FSL.

Alternatively, each of the light sensing pixels LSP may be connected to one of the display scan lines GL in units of horizontal lines. The respective light sensing pixels LSP may generate light sensing signals corresponding to the amount of reflected light incident from the front direction, and output the light sensing signals to the light sensing lines ERL in response to the display scan signals input through the display scan lines GL.

The display scan driver 110 may be disposed in the non-display area NDA. It has been illustrated that the display scan driver 110 is disposed on one side (e.g., the left side) of the display panel 100, but the present disclosure is not limited to that illustrated in FIG. 5. For example, the display scan driver 110 may be provided in plural on both sides (e.g., left and right sides) of the display panel 100.

The display scan driver 110 may be electrically connected to the main driving circuit 200 through the gate control lines GCL. The display scan driver 110 receives scan control signals from the main driving circuit 200, sequentially generates display scan signals in units of horizontal line driving periods according to the scan control signals, and sequentially supplies the display scan signals to the display scan lines GL. In addition, the display scan driver 110 may sequentially generate emission control signals according to the scan control signals from the main driving circuit 200 and sequentially supply the emission control signals to the emission control lines VL.

The gate control lines GCL may extend from the main driving circuit 200 to the display scan driver 110 according to a position where the display scan driver 110 is disposed. The gate control lines GCL may supply the scan control signals received from the main driving circuit 200 to the display scan driver 110.

The light sensing scan driver 120 may be disposed in a portion of the non-display area NDA different from a portion of the non-display area NDA in which the display scan driver 110 is disposed. It has been illustrated in FIG. 5 that the light sensing scan driver 120 is disposed on the other side (e.g., the right side) of the display panel 100, but the present disclosure is not limited thereto. The light sensing scan driver 120 may be electrically connected to the main driving circuit 200 through the light sensing control lines SCL. The light sensing scan driver 120 receives light sensing control signals from the main driving circuit 200 and sequentially generates reset control signals and light sensing scan signals in units of horizontal line driving periods according to the light sensing control signals. In addition, the light sensing scan driver 120 sequentially supplies the sequentially generated reset control signals to the sensing reset lines REL. In addition, the light sensing scan driver 120 may sequentially generate the light sensing scan signals according to the light sensing control signals from the main driving circuit 200 and sequentially supply the light sensing scan signals to the light sensing scan lines FSL.

The light sensing control lines SCL may extend from the main driving circuit 200 to the light sensing scan driver 120 according to a position where the light sensing scan driver 120 is disposed. The light sensing control lines SCL may supply the light sensing control signals received from the main driving circuit 200 to the light sensing scan driver 120.

The sub-area SBA may include the main driving circuit 200, a display pad area DPA, and first and second touch pad areas TPA1 and TPA2. The display pad area DPA, the first touch pad area TPA1, and the second touch pad area TPA2 may be disposed at an edge of the sub-area SBA. The display pad area DPA, the first touch pad area TPA1, and the second touch pad area TPA2 may be electrically connected to the circuit board 300 using an anisotropic conductive layer or a low-resistance high-reliability material such as a self assembly anisotropic conductive paste (SAP).

The fan-out lines FOL may extend from the main driving circuit 200 to the display area DA. In addition, the fan-out lines FOL are connected to the main driving circuit 200 and the plurality of data lines DL so that the data voltages received from the main driving circuit 200 may be supplied to the plurality of data lines DL, respectively.

The main driving circuit 200 may output signals and voltages for driving the display panel 100 to the fan-out lines FOL. The main driving circuit 200 may supply the data voltages to the data lines DL through the fan-out lines FOL. The data voltages may be supplied to the plurality of display pixels SP, and may determine a luminance of the display pixels SP. The main driving circuit 200 may supply the scan control signals to the display scan driver 110 through the gate control lines GCL. The main driving circuit 200 may generate digital video data according to touch coordinates based on touch coordinate data from the touch driving circuit 400 or execute an application indicated by an icon displayed at user's touch coordinates.

Figure 6:
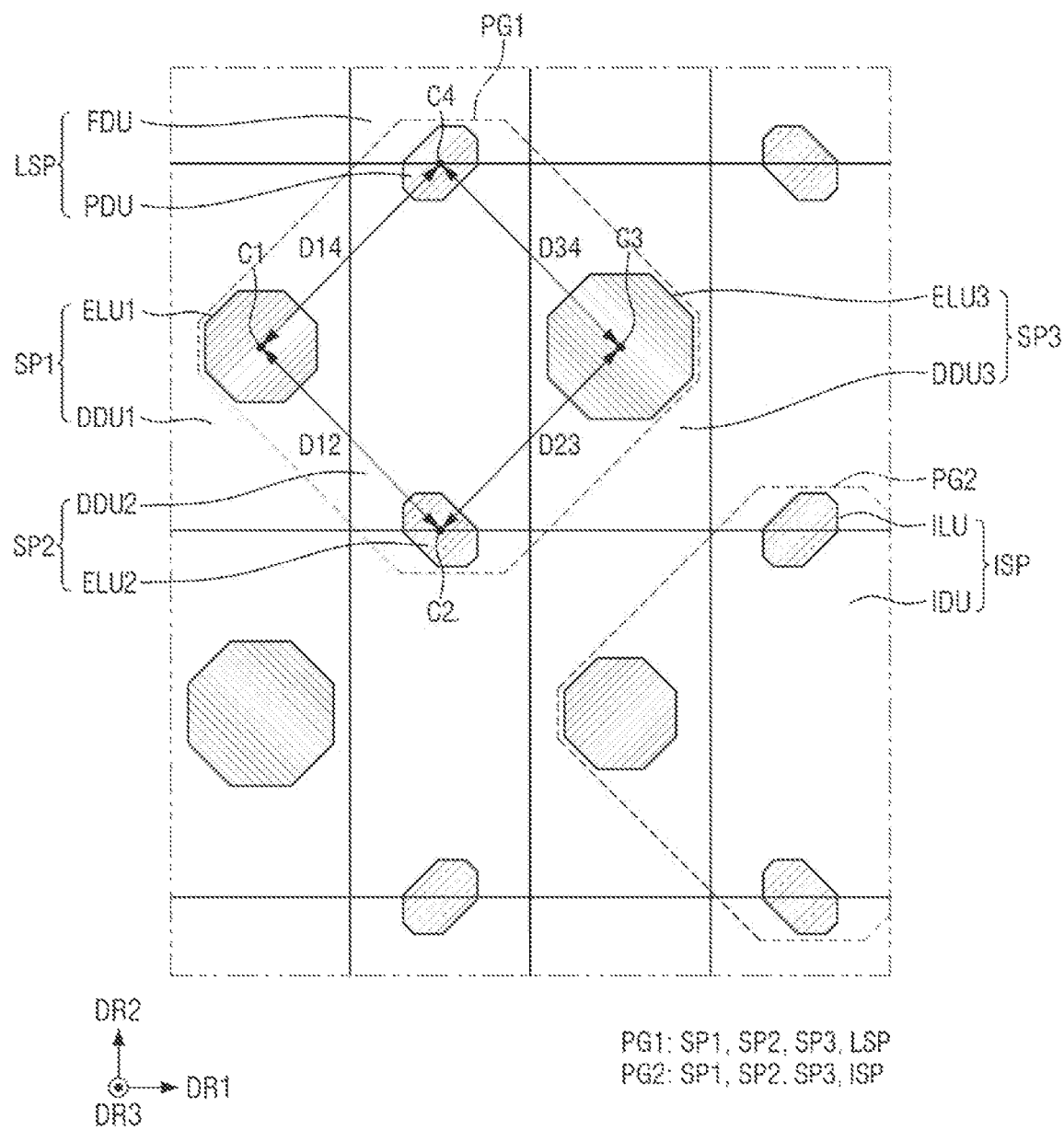
FIG. 6 is a layout diagram illustrating a display area according to an embodiment of the present disclosure.

FIG. 6 is a layout diagram illustrating a display area according to an embodiment of the present disclosure.

Referring to FIG. 6, the display area DA may include display pixels SP, infrared light emitting pixels ISP, and light sensing pixels LSP. Here, the display pixels SP may be divided into first display pixels SP1, second display pixels SP2, and third display pixels SP3.

Each of the light sensing pixels LSP including the first display pixel SP1, the second display pixel SP2, and the third display pixel SP3 may be respectively referred to as a first unit pixel PG1. Additionally, each of the infrared light emitting pixels ISP including the first display pixel SP1, the second display pixel SP2, and the third display pixel SP3 may be respectively referred to as a second unit pixel PG2.

Each of the first and second unit pixels PG1 and PG2 may be referred to as display pixels of a minimum unit capable of displaying a white color, and each of the first unit pixels PG1 may sense light. The first unit pixels PG1 and the second unit pixels PG2 may be alternately arranged in a zigzag pattern on a plane, and may be arranged in a matrix form in one diagonal direction. In addition, the first unit pixels PG1 and the second unit pixels PG2 may alternate in a horizontal or vertical stripe form to be arranged in a matrix form.

The first display pixel SP1 may include a first light emitting unit ELU1 for emitting first light and a first pixel driver DDU1 for applying a driving current to a light emitting element of the first light emitting unit ELU1. The first light may be light of a red wavelength band. For example, a main peak wavelength of the first light may be positioned between approximately 600 nm and 750 nm.

The second display pixel SP2 may include a second light emitting unit ELU2 for emitting second light and a second pixel driver DDU2 for applying a driving current to a light emitting element of the second light emitting unit ELU2. The second light may be light of a blue wavelength band. For example, a main peak wavelength of the second light may be positioned between approximately 370 nm and 460 nm.

The third display pixel SP3 may include a third light emitting unit ELU3 for emitting third light and a third pixel driver DDU3 for applying a driving current to a light emitting element of the third light emitting unit ELU3. The third light may be light of a green wavelength band. For example, a main peak wavelength of the third light may be positioned between approximately 480 nm and 560 nm.

The infrared light emitting pixel ISP may include an infrared light emitting unit ILU that emits light in an infrared wavelength band and an infrared pixel driver IDU for applying a driving current to the light emitting element of the infrared light emitting unit ILU. The main peak wavelength of infrared light may be located between approximately 750 nm and 1 mm.

The light sensing pixel LSP includes a light sensing unit PDU and a sensing driver FDU.

In a first unit pixel PG1, the first to third pixel drivers DDU1 to DDU3 may be arranged in a preset order in the first direction DR1. Alternatively, any one of the first to third pixel drivers DDU1 to DDU3 may be disposed in the first direction DR1 with another adjacent pixel driver. In addition, the sensing driver FDU may be disposed in the first direction DR1 of any one of the first to third pixel drivers DDU1 to DDU3. Alternatively, the sensing driver FDU may be disposed in the second direction DR2 of any one of the first to third pixel drivers DDU1 to DDU3.

The first pixel drivers DDU1 adjacent to each other in a data line direction may be disposed in the second direction DR2. The second pixel drivers DDU2 adjacent to each other in the direction of the data line DL may be disposed in the second direction DR2. Similarly, all of the sensing drivers FDU adjacent to each other in the direction of the data line DL may also be disposed in the second direction DR2.

The first light emitting unit ELU1, the second light emitting unit ELU2, the third light emitting unit ELU3, the infrared light emitting unit ILU, and the light sensing unit PDU may have a rectangular, octagonal, or rhombus planar shape, but are not limited thereto. The first light emitting unit ELU1, the second light emitting unit ELU2, the third light emitting unit ELU3, the infrared light emitting unit ILU, and the light sensing unit PDU may have a flat shape of a polygon other than a rectangle, an octagon, and a rhombus.

Depending on positions where the first light emitting unit ELU1, the second light emitting unit ELU2, the third light emitting unit ELU3, and the light sensing unit PDU are disposed and shapes of the first light emitting unit ELU1, the second light emitting unit ELU2, the third light emitting unit ELU3, and the light sensing unit PDU in a plan view, a distance D12 between the center C1 of the first light emitting unit ELU1 and the center C2 of the second light emitting unit ELU2 neighboring each other, a distance D23 between the center C2 of the second light emitting unit ELU2 and the center C3 of the third light emitting unit ELU3 neighboring each other, a distance D14 between the center C1 of the first light emitting unit ELU1 and the center C4 of the light sensing unit PDU neighboring each other in another direction, and a distance D34 between the center C4 of the light sensing unit PDU and the center C3 of the third light emitting unit ELU3 neighboring each other may be substantially the same as each other.

Figure 7:
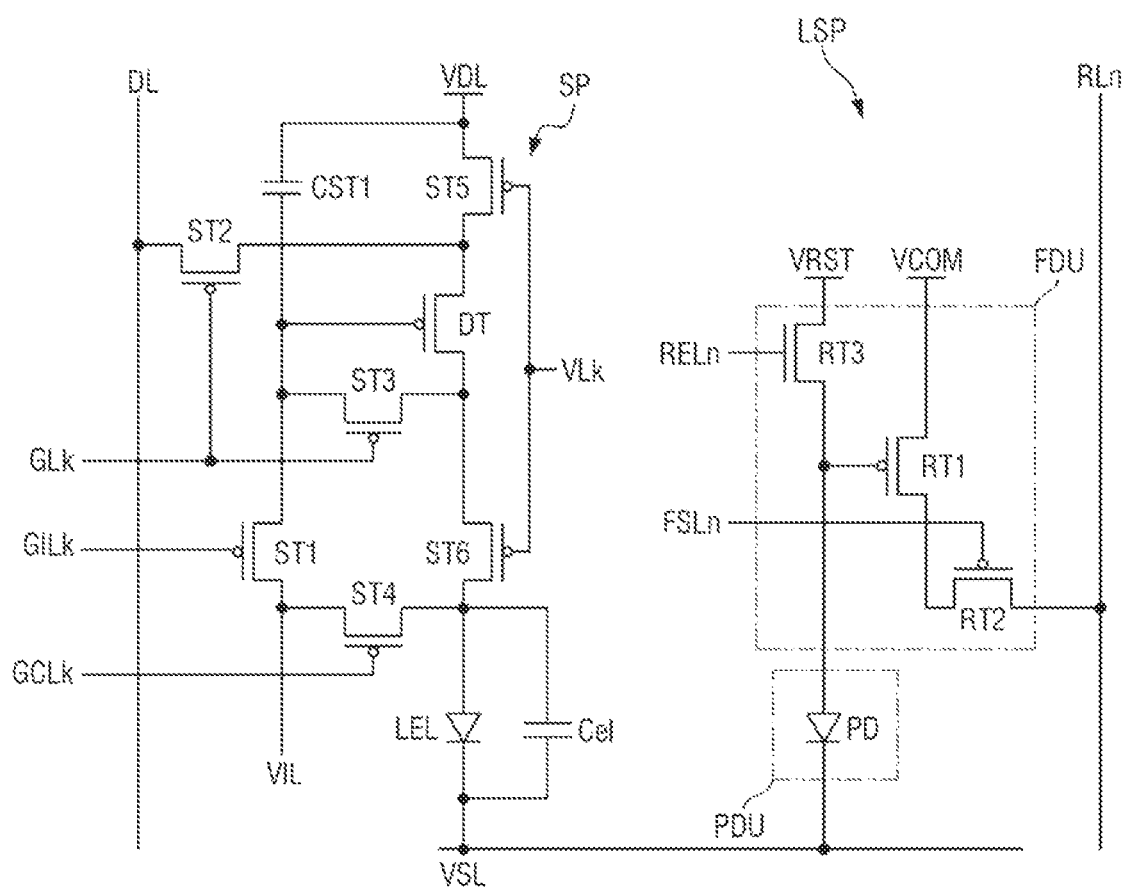
FIG. 7 is a circuit diagram illustrating a display pixel and a light sensing pixel according to an embodiment of the present disclosure.

FIG. 7 is a circuit diagram illustrating the display pixel and the light sensing pixel according to an embodiment of the present disclosure.

Referring to FIG. 7, each display pixel SP according to an embodiment may be connected to a k-th display initialization line GILk, a k-th display scan line GLk, a k-th display control line GCLk, and a k-th emission control line VLK. In addition, the display pixel SP may be connected to a first driving voltage line VDL to which a first driving voltage is supplied, a second driving voltage line VSL to which a second driving voltage is supplied, and a third driving voltage line VIL to which a third driving voltage is supplied. Hereinafter, k and are positive integers excluding 0.

The display pixel SP may include a light emitting unit ELU and a pixel driving unit DDU. The light emitting unit ELU may include a light emitting element LEL. The pixel driving unit DDU may include a driving transistor DT, switch elements, and a capacitor CST1. The switch elements include first to sixth transistors ST1, ST2, ST3, ST4, ST5, and ST6.

The driving transistor DT may include a gate electrode, a first electrode, and a second electrode. The driving transistor DT controls a drain-source current (hereinafter, referred to as a "driving current") Ids flowing between the first electrode and the second electrode according to a data voltage applied to the gate electrode. The driving current Ids flowing through a channel of the driving transistor DT is proportional to the square of a difference between a voltage Vsg between the first electrode and the gate electrode and a threshold voltage of the driving transistor DT as represented in Equation 1.

$$Ids = k' \times (Vsg - Vth)^2 \qquad \text{[Equation 1]}$$

Here, k' refers to a proportional coefficient determined by a structure and physical characteristics of the driving transistor DT, Vsg refers to the voltage between the first electrode and the gate electrode of the driving transistor DT, and Vth refers to the threshold voltage of the driving transistor DT.

The light emitting element LEL emits light according to the driving current Ids. The larger the driving current Ids, the larger the amount of light emitted from the light emitting element LEL.

The light emitting element LEL may be an organic light emitting diode including an organic light emitting layer disposed between an anode electrode and a cathode electrode. Alternatively, the light emitting element LEL may be an inorganic light emitting element including an inorganic semiconductor disposed between an anode electrode and a cathode electrode. Alternatively, the light emitting element LEL may be a quantum dot light emitting element including a quantum dot light emitting layer disposed between an anode electrode and a cathode electrode. Alternatively, the light emitting element LEL may be a micro light emitting element including a micro light emitting diode disposed between an anode electrode and a cathode electrode.

The anode electrode of the light emitting element LEL may be connected to a first electrode of the fourth transistor ST4 and a second electrode of the sixth transistor ST6, and the cathode electrode of the light emitting element LEL may be connected to the second driving voltage line VSL. A parasitic capacitance Cel may be formed between the anode electrode and the cathode electrode of the light emitting element LEL.

The first transistor ST1 is turned on by an initialization scan signal of the k-th display initialization line GILk to connect the gate electrode of the driving transistor DT to the third driving voltage line VIL. Accordingly, a third driving voltage of the third driving voltage line VIL may be applied to the gate electrode of the driving transistor DT. A gate electrode of the first transistor ST1 may be connected to the k-th display initialization line GILk, a first electrode of the first transistor ST1 may be connected to the gate electrode of the driving transistor DT, and a second electrode of the first transistor ST1 may be connected to the third driving voltage line VIL.

The second transistor ST2 is turned on by a display scan signal of the k-th display scan line GLk to connect the first electrode of the driving transistor DT to the data line DL. Accordingly, the data voltage of the data line DL may be applied to the first electrode of the driving transistor DT. A gate electrode of the second transistor ST2 may be connected to the k-th display scan line GLk, a first electrode of the second transistor ST2 may be connected to the first electrode of the driving transistor DT, and a second electrode of the second transistor ST2 may be connected to the data line DL.

The third transistor ST3 is turned on by the display scan signal of the k-th display scan line GLk to connect the gate electrode and the second electrode of the driving transistor DT to each other. When the gate electrode and the second electrode of the driving transistor DT are connected to each other, the driving transistor DT is driven as a diode. A gate electrode of the third transistor ST3 may be connected to the k-th display scan line GLk, a first electrode of the third transistor ST3 may be connected to the second electrode of the driving transistor DT, and a second electrode of the third transistor ST3 may be connected to the gate electrode of the driving transistor DT.

The fourth transistor ST4 is turned on by a display control signal of the k-th display control line GCLk to connect the anode electrode of the light emitting element LEL to the third driving voltage line VIL. The third driving voltage of the third driving voltage line VIL may be applied to the anode electrode of the light emitting element LEL. A gate electrode of the fourth transistor ST4 may be connected to the k-th display control line GCLk, the first electrode of the fourth transistor ST4 may be connected to the anode electrode of the light emitting element LEL, and a second electrode of the fourth transistor ST4 may be connected to the third driving voltage line VIL.

The fifth transistor ST5 is turned on by an emission signal of the k-th emission control line VLk to connect the first electrode of the driving transistor DT to the first driving voltage line VDL. A gate electrode of the fifth transistor ST5 may be connected to the k-th emission control line VLk, a first electrode of the fifth transistor ST5 may be connected to the first driving voltage line VDL, and a second electrode of the fifth transistor ST5 may be connected to the first electrode of the driving transistor DT.

The sixth transistor ST6 is disposed between the second electrode of the driving transistor DT and the anode electrode of the light emitting element LEL. The sixth transistor ST6 is turned on by an emission control signal of the k-th emission control line VLk to connect the second electrode of the driving transistor DT to the anode electrode of the light emitting element LEL. A gate electrode of the sixth transistor ST6 may be connected to the k-th emission control line VLK, a first electrode of the sixth transistor ST6 may be connected to the second electrode of the driving transistor DT, and the second electrode of the sixth transistor ST6 may be the anode electrode of the light emitting element LEL.

When both the fifth transistor ST5 and the sixth transistor ST6 are turned on, the driving current Ids of the driving transistor DT according to the data voltage applied to the gate electrode of the driving transistor DT may flow to the light emitting element LEL.

The capacitor CST1 is formed between the gate electrode of the driving transistor DT and the first driving voltage line VDL. A first capacitor electrode of the capacitor CST1 may be connected to the gate electrode of the driving transistor DT, and a second capacitor electrode of the capacitor CST1 may be connected to the first driving voltage line VDL.

When the first electrode of each of the first to sixth transistors ST1, ST2, ST3, ST4, ST5, and ST6 and the driving transistor DT is a source electrode, the second electrode of each of the first to sixth transistors ST1, ST2, ST3, ST4, ST5, and ST6 and the driving transistor DT may be a drain electrode. Alternatively, when the first electrode of each of the first to sixth transistors ST1, ST2, ST3, ST4, ST5, and ST6 and the driving transistor DT is a drain electrode, the second electrode of each of the first to sixth transistors ST1, ST2, ST3, ST4, ST5, and ST6 and the driving transistor DT may be a source electrode.

An active layer of each of the first to sixth transistors ST1, ST2, ST3, ST4, ST5, and ST6 and the driving transistor DT may be formed of any one of polysilicon, amorphous silicon, and an oxide semiconductor. It has been mainly described in FIG. 7 that the first to sixth transistors ST1, ST2, ST3, ST4, ST5, and ST6, and the driving transistor DT are formed as P-type metal oxide semiconductor field effect transistors (MOSFETs), but the present disclosure is not limited thereto. For example, the first to sixth transistors ST1, ST2, ST3, ST4, ST5, and ST6, and the driving transistor DT may also be formed as N-type MOSFETs. Alternatively, at least one of the first to sixth transistors ST1, ST2, ST3, ST4, ST5, and ST6 may be formed as an N-type MOSFET.

Each of the light sensing pixels LSP is electrically connected to an n-th sensing reset line RELn, an n-th light sensing scan line FSLn, and an n-th light sensing line RLn. Each of the light sensing pixels LSP may be reset by a reset signal from the n-th sensing reset line RELn, and may transmit a light sensing signal to each of the n-th light sensing lines RLn in response to a sensing scan signal from the n-th light sensing scan line FSLn.

Each of the light sensing pixels LSP may be divided into a light sensing unit PDU including a light sensing element PD and a sensing driver FDU including first to third sensing transistors RT1 to RT3 and a sensing capacitor. Here, the sensing capacitor may be formed in a parallel with the light sensing element PD.

The first sensing transistor RT1 of the sensing driver FDU may make a light sensing current flow according to a voltage of the light sensing element PD and the sensing capacitor. An amount of the light sensing current may change depending on a voltage applied to the light sensing element PD and the sensing capacitor. A gate electrode of the first sensing transistor RT1 may be connected to a second electrode of the light sensing element PD. A first electrode of the first sensing transistor RT1 may be connected to a common voltage source VCOM to which a common voltage is applied. A second electrode of the first sensing transistor RT1 may be connected to a first electrode of the second sensing transistor RT2.

The second sensing transistor RT2 may make the sensing current of the first sensing transistor RT1 flow to the n-th light sensing line RLn when a sensing scan signal of a gate-on voltage is applied to the n-th light sensing scan line FSLn. In this case, the n-th light sensing line RLn may be charged with a sensing voltage by the sensing current. A gate electrode of the second sensing transistor RT2 may be connected to the n-th light sensing scan line FSLn, the first electrode of the second sensing transistor RT2 may be connected to the second electrode of the first sensing transistor RT1, and a second electrode of the second sensing transistor RT2 may be connected to the n-th light sensing line RLn.

The third sensing transistor RT3 may reset the voltage of the light sensing element PD and the sensing capacitor to a reset voltage of a reset voltage source VRST when a reset signal of a gate-on voltage is applied to the n-th sensing reset line RELn. A gate electrode of the third sensing transistor RT3 may be connected to the n-th sensing reset line RELn, a first electrode of the third sensing transistor RT3 may be connected to the reset voltage source VRST, and a second electrode of the third sensing transistor RT3 may be connected to the second electrode of the light sensing element PD.

It has been mainly described in FIG. 7 that the first sensing transistor RT1 and the second sensing transistor RT2 are formed as P-type MOSFETs and the third sensing transistor RT3 is formed as an N-type MOSFET, but an embodiment of the present disclosure is not limited thereto, and the first to third sensing transistors RT1 to RT3 may be selectively formed as the same type MOSFET or different type MOSFETs. In addition, one of the first electrode and the second electrode of each of the first sensing transistor RT1, the second sensing transistor RT2, and the third sensing transistor RT3 may be a source electrode and the other of the first electrode and the second electrode of each of the first sensing transistor RT1, the second sensing transistor RT2, and the third sensing transistor RT3 may be a drain electrode.

Figure 8:
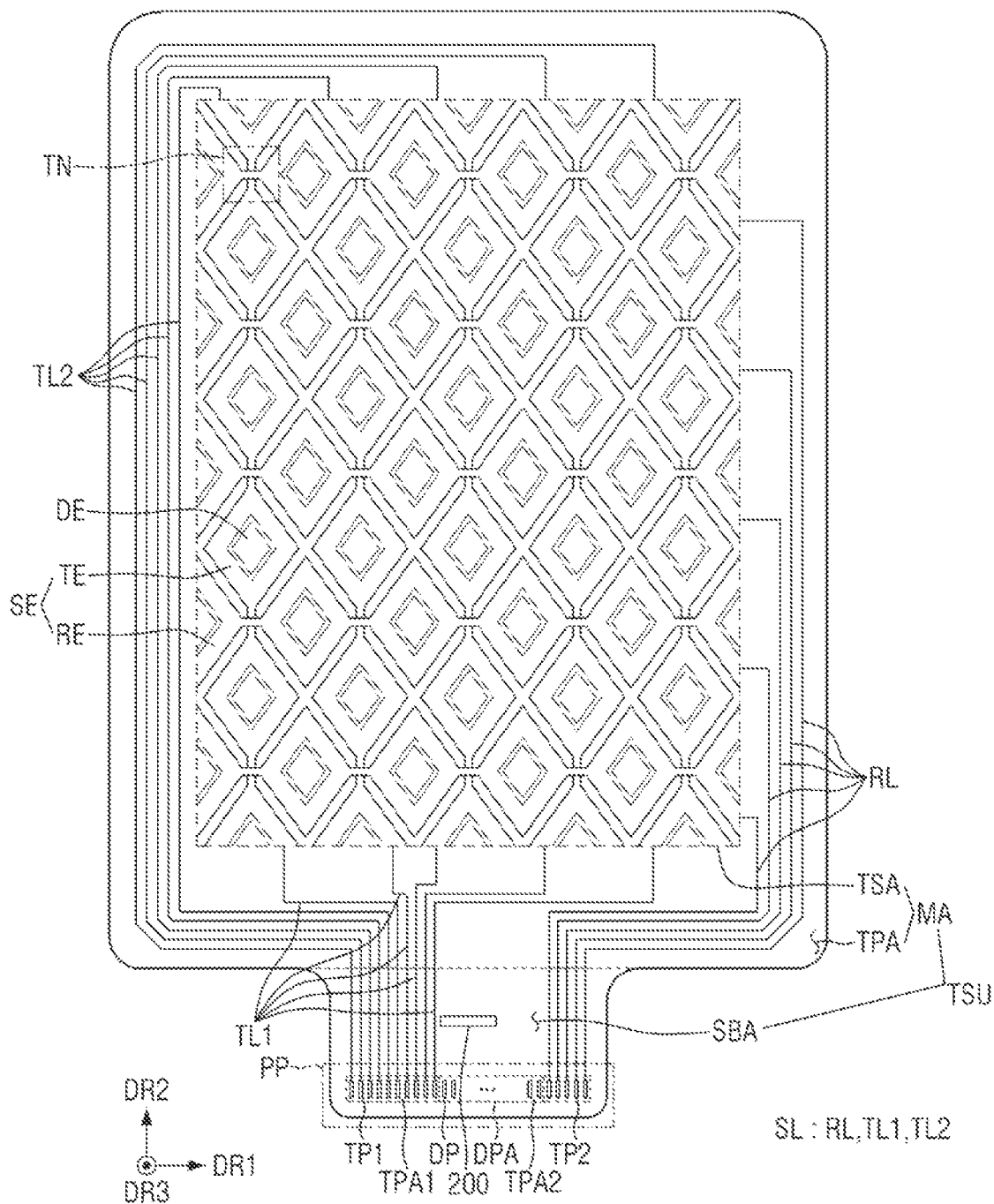
FIG. 8 is a schematic layout diagram illustrating an example of a touch sensing unit illustrated in FIG. 3.

FIG. 8 is a schematic layout diagram illustrating an example of a touch sensing unit illustrated in FIG. 3.

It will be mainly described in FIG. 8 that touch electrodes SE of a main area MA include two types of electrodes, for example, driving electrodes TE and sensing electrodes RE and are driven in a mutual capacitive manner by sensing a charge change amount in mutual capacitance of each of a plurality of touch nodes TN through the sensing electrodes RE after applying touch driving signals to the driving electrodes TE, but the present disclosure is not limited thereto.

In FIG. 8, for convenience of explanation, only the driving electrodes TE, the sensing electrodes RE, dummy electrodes DE, touch lines SL, and first and second touch pads TP1 and TP2 have been illustrated.

The main area MA of the touch sensing unit TSU includes a touch sensing area TSA for sensing a user's touch and a touch peripheral area TPA disposed around the touch sensing area TSA. The touch sensing area TSA may overlap the display area DA of FIGS. 1 to 3, and the touch peripheral area TPA may overlap the non-display area NDA of FIGS. 1 to 3.

The driving electrodes TE, the sensing electrodes RE, and the dummy electrodes DE are disposed in the touch sensing area TSA. The driving electrodes TE and the sensing electrodes RE may be electrodes for forming mutual capacitance to sense a touch of an object or a person.

The sensing electrodes RE may be arranged in parallel in the first direction DR1 and the second direction DR2. The sensing electrodes RE may be electrically connected to each other in the first direction DR1. The sensing electrodes RE adjacent to each other in the first direction DR1 may be connected to each other. The sensing electrodes RE adjacent to each other in the second direction DR2 may be electrically disconnected from each other. Accordingly, the touch node TN where mutual capacitance is formed may be disposed at each of intersection parts between the driving electrodes TE and the sensing electrodes RE. The plurality of touch nodes TN may correspond to the intersection parts between the driving electrodes TE and the sensing electrodes RE.

The driving electrodes TE may be arranged in parallel in the first direction DR1 and the second direction DR2. The driving electrodes TE adjacent to each other in the first direction DR1 may be electrically disconnected from each other. The driving electrodes TE may be electrically connected to each other in the second direction DR2. The driving electrodes TE adjacent to each other in the second direction DR2 may be connected to each other through a separate connection electrode.

Each of the dummy electrodes DE may be surrounded by the driving electrode TE or the sensing electrode RE. Each of the dummy electrodes DE may be electrically disconnected from the driving electrode TE or the sensing electrode RE. Each of the dummy electrodes DE may be spaced apart from the driving electrode TE or the sensing electrode RE. Each of the dummy electrodes DE may be electrically floated.

It has been illustrated in FIG. 8 that each of the driving electrodes TE, the sensing electrodes RE, and the dummy electrodes DE has a rhombic shape in a plan view, but the present disclosure is not limited thereto. For example, each of the driving electrodes TE, the sensing electrodes RE, and the dummy electrodes DE may have a rectangular shape other than the rhombic shape, polygonal shapes other than the rectangular shape or the rhombic shape, a circular shape, or an elliptical shape in a plan view.

The touch lines SL may be disposed in the touch peripheral area TPA. The touch lines SL may include first touch driving lines TL1 and second touch driving lines TL2 connected to the driving electrodes TE and touch sensing lines RL connected to the sensing electrodes RE.

The respective sensing electrodes RE disposed at one end of the touch sensing area TSA may be connected to the touch sensing lines RL in a one-to-one manner. For example, as illustrated in FIG. 8, the respective sensing electrodes RE disposed at a right end among the sensing electrodes RE electrically connected to each other in the first direction DR1 may be connected to the respective touch sensing lines RL. In addition, the respective touch sensing lines RL may be connected to the second touch pads TP2 disposed in a pad part PP in one-to-one manner.

The driving electrodes TE disposed at one end of the touch sensing area TSA may be connected to the first touch driving lines TL1 in a one-to-one manner, and the driving electrodes TE disposed at the other end of the touch sensing area TSA may be connected to the second touch driving lines TL2 in a one-to-one manner. For example, the driving electrodes TE disposed at a lower end among the driving electrodes TE electrically connected to each other in the second direction DR2 may be connected to the first touch driving lines TL1, respectively, and the driving electrodes TE disposed at an upper end among the driving electrodes TE electrically connected to each other in the second direction DR2 may be connected to the second touch driving lines TL2, respectively. The second touch driving lines TL2 may be connected to the driving electrodes TE on the upper side of the touch sensing area TSA via the outer left side of the touch sensing area TSA The first touch driving lines TL1 and the second touch driving lines TL2 may be connected to first touch pads TP1 disposed in the pad part PP in a one-to-one manner. The driving electrodes TE are connected to the first and second touch driving lines TL1 and TL2 on both sides of the touch sensing area TSA to receive touch driving signals. Accordingly, it is possible to prevent a difference between the touch driving signals applied to the driving electrodes TE disposed on the lower side of the touch sensing area TSA and the touch driving signals applied to the driving electrodes TE disposed on the upper side of the touch sensing area TSA from occurring due to an RC delay of the touch driving signals.

Figure 9:
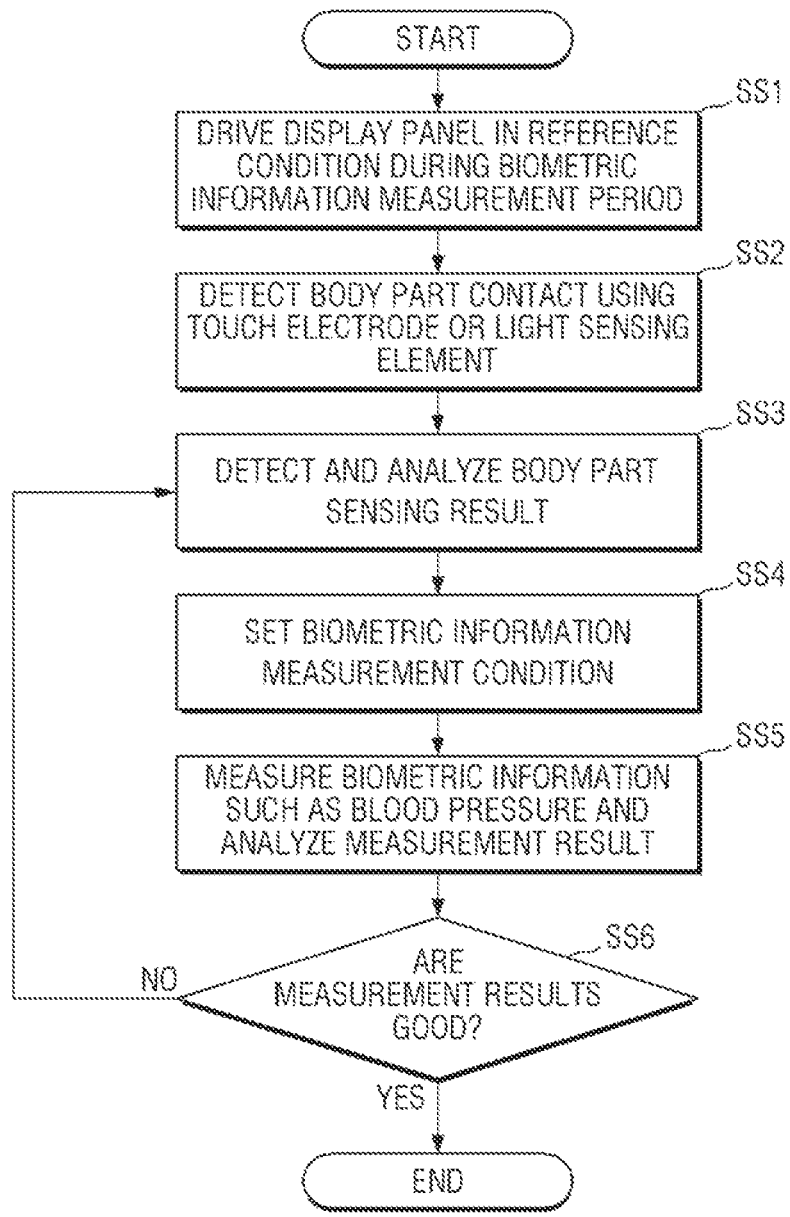
FIG. 9 is a flowchart illustrating a method for measuring biometric information according to an embodiment of the present disclosure.

FIG. 9 is a flowchart illustrating a method for measuring biometric information according to an embodiment of the present disclosure.

Referring to FIG. 9, to detect the user's touch area during the period for measuring biometric information such as blood pressure, the main driving circuit 200 selects one of preset reference conditions and receives a control signal according to the reference condition (SS1) In other words, the display panel 100 is driven in a preset reference condition in the biometric information measurement period.

For example, the main driving circuit 200 may select a first reference condition among the preset reference conditions and control a touch detection operation of the touch driving circuit 400. For example, the main driving circuit 200 may transmit a touch sensing control signal to the touch driving circuit 400 according to the first reference condition to control a touch sensing operation of the touch driving circuit 400.

Alternatively, the main driving circuit 200 may select a second reference condition among the preset reference conditions and detect the user's touch area through the light sensing pixels LSP. For example, the main driving circuit 200 may transmit a scan control signal to the display scan driver 110 and the light sensing scan driver 120 and control signal outputs of the display scan driver 110 and the light sensing scan driver 120, and detect a user's touch area through the light sensing pixels LSP.

On the other hand, the main driving circuit 200 may select a third reference condition among the preset reference conditions and control a touch sensing operation of the touch driving circuit 400 using the pressure sensing unit PSU. The main driving circuit 200 may transmit a pressure sensing control signal to the touch driving circuit 400 according to the third reference condition to control the touch sensing operation of the touch driving circuit 400. The touch driving circuit 400 may sense a user's touch area through lower electrodes and upper electrodes of the pressure sensing unit PSU in response to a pressure sensing control signal inputted during the biometric information measurement period.

The main driving circuit 200 detects a user's touch area through the light sensing pixels LSP according to any one of the preset reference conditions and generates touch coordinate data corresponding to the touch area, or controls the touch driving circuit 400 to receive touch coordinate data corresponding to the user's touch position and touch area (SS2). In other words, in SS2, body part contact is detected using a touch electrode or a light sensing element.

For example, the main driving circuit 200 may transmit a touch sensing control signal to the touch driving circuit 400 according to the first reference condition among the preset reference conditions. Accordingly, the touch driving circuit 400 supplies a touch driving signal to the driving electrodes TE among the touch electrodes SE in response to the touch sensing control signal provided from the main driving circuit 200. In addition, touch coordinate data corresponding to the user's touch position and touch area are generated by receiving sensing signals fed back from the driving electrodes TE and touch sensing signals detected from the sensing electrodes RE. The touch driving circuit 400 transmits touch coordinate data to the main driving circuit 200 in real time.

Alternatively, the main driving circuit 200 transmits a scan control signal to the display scan driver 110 and the light sensing scan driver 120 according to the second reference condition among the preset reference conditions, and data voltages having a preset voltage magnitude may be supplied to the data lines DL. Accordingly, the display scan driver 110 and the light sensing scan driver 120 may sequentially drive the light sensing pixels LSP, and the main driving circuit 200 may detect a user's touch position and touch areas by receiving light sensing signals through the light sensing pixels LSP. In this case, the main driving circuit 200 may generate touch coordinate data corresponding to the user's touch position and touch areas by comparing and analyzing the voltage magnitude change of the light sensing signals. In other words, the main driving circuit 200 can generate touch coordinate data about the user's touch position and touch area by analyzing the voltage changes in the light sensing signals.

The main driving circuit 200 detects touch area information including touch position, touch shape, and touch area of a user's body part by analyzing touch coordinate data generated or received according to at least one of the preset reference conditions (SS3). In other words, in SS3, the body part sensing result is detected and analyzed.

The main driving circuit 200 individually or sequentially analyzes the touch position, touch shape, and touch area of the body part in the display area DA through the touch coordinate data. In addition, a touch area information including information about the touch position, touch shape, touch area and the like of a body part may be stored as digital data.

The main driving circuit 200 sets a biometric information measurement area using touch area information of a user's body part, and subdivides and sets biometric information measurement conditions (SS4).

For example, the main driving circuit 200 determines and sets the biometric information measurement period for the touch area of the user's body part according to the touch area information of the user's body part. In this case, the biometric information measurement area is determined by dividing it into an emission area and a light sensing area. The emission color and luminance (or emission wavelength band) of display pixels SP or infrared light emitting pixels ISP included in the emission area (e.g., the light emitting area) may be determined.

Subsequently, the main driving circuit 200 drives the display pixels SP or the infrared light emitting pixels ISP included in the emission area of the biometric information measurement area, and receives light sensing signals through light sensing pixels LSP included in the light sensing area of the biometric information measurement area to measure the biometric information such as a user's blood pressure (SS5).

For example, the main driving circuit 200 supplies a data voltage to at least one data line DL. In this case, pixels emitting infrared light or emission color that are determined in real time among the display pixels SP and the infrared light emitting pixels ISP may emit light with a luminance or wavelength band that is also determined in real time. In addition, driving of the display scan driver 110 and the light sensing scan driver 120 is sequentially controlled. Additionally, the main driving circuit 200 receives the light sensing signal inputted through at least one light sensing line ERL among the light sensing lines ERL.

The main driving circuit 200 may calculate a pulse wave signal reflecting blood change according to the user's heartbeat by using the light sensing signals received through the light sensing pixels LSP of the light sensing area, thereby measuring biometric information such as a user's blood pressure according to the magnitude and change period of the pulse wave signal.

The main driving circuit 200 compares the user's biometric information such as the user's blood pressure, which is measured in real time, with previously stored biometric information or data of a reference value, and determines whether the biometric information is valid or whether to re-measure according to the comparison result (SS6).

The main driving circuit 200 may generate result image data according to the biometric information measurement results measured in real time, and display the result image data on the display panel 100 as an image.

Figure 10:
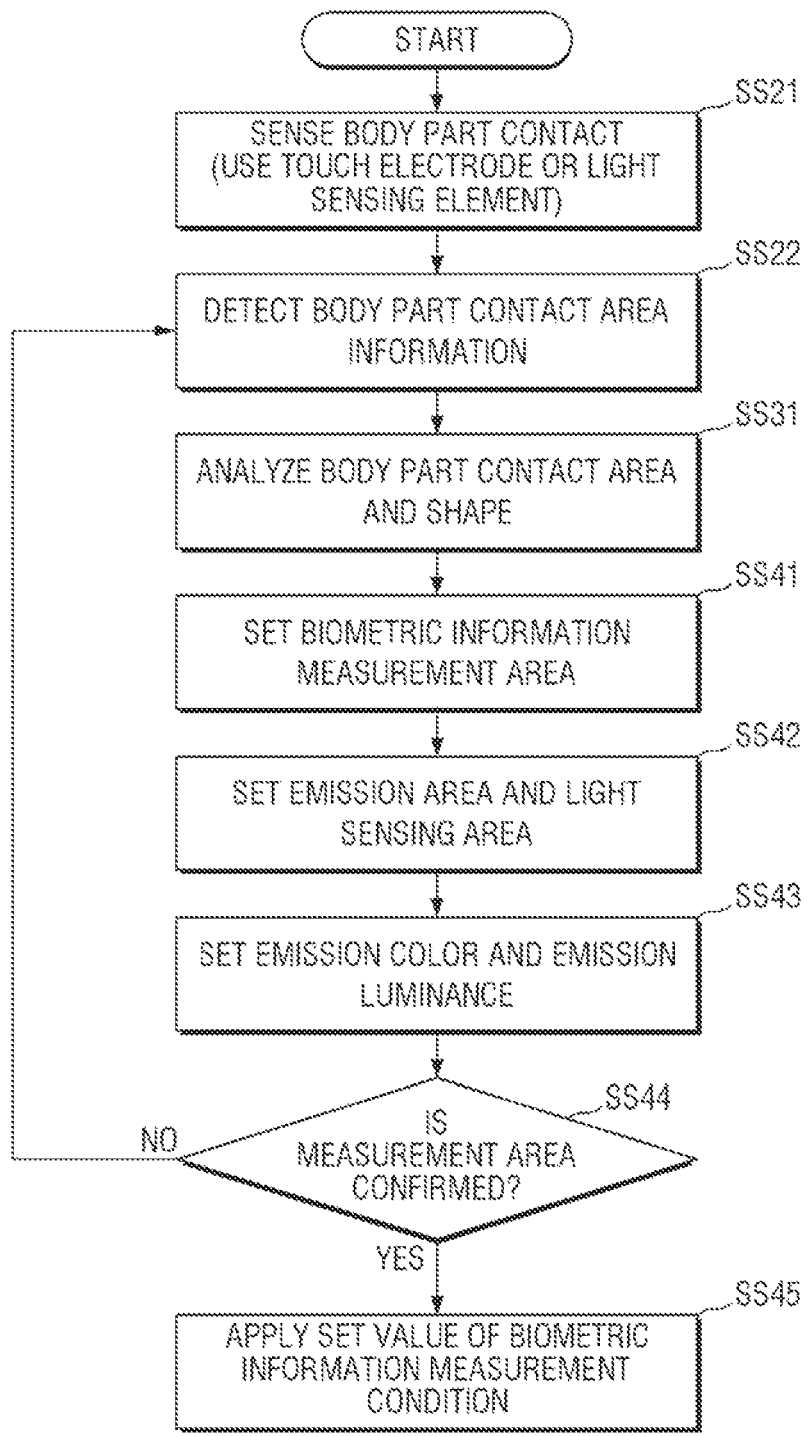
FIG. 10 is a flowchart illustrating a method of detecting body part touch, a method of deriving detection results, and a method of setting detection conditions of FIG. 9 step by step.

FIG. 10 is a flowchart illustrating a method of detecting body part touch, a method of deriving detection results, and a method of setting detection conditions of FIG. 9 step by step. Further, FIG. 11 is a diagram showing an image display screen and body part touch area detection process during a biometric information measurement period.

Figure 11:
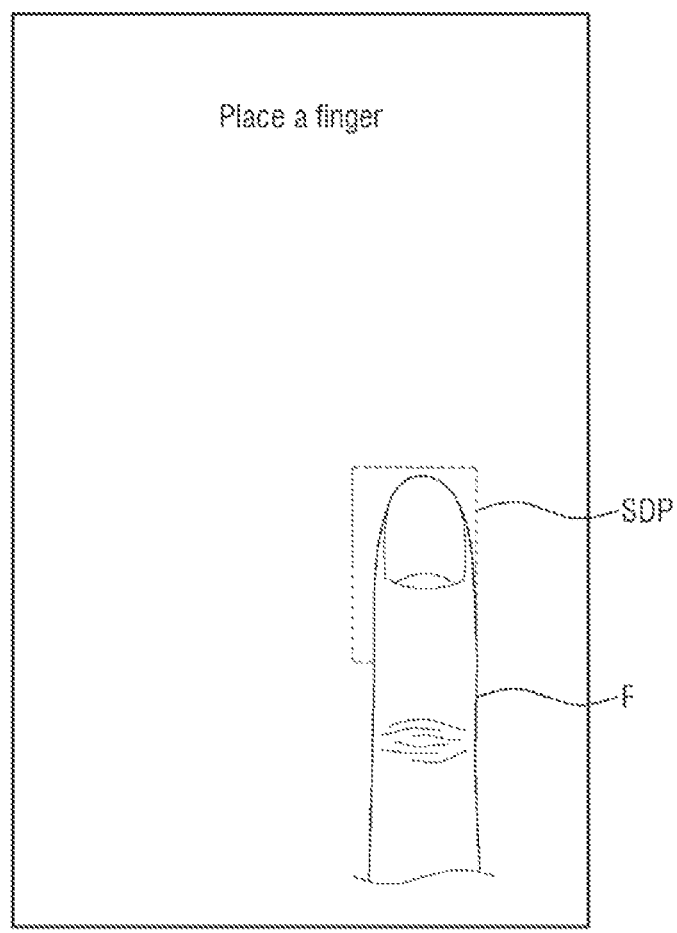
FIG. 11 is a diagram showing an image display screen and a body part touch area detection process during a biometric information measurement period.

Referring to FIGS. 10 and 11, the main driving circuit 200 transmits a touch sensing control signal to the touch driving circuit 400 according to a first reference condition among the preset reference conditions, and controls a touch sensing operation of the touch driving circuit 400 (SS21). In other words, in SS21, body part contact may be sensed.

The touch driving circuit 400 sequentially supplies a touch driving signal to the driving electrodes TE of the touch sensing unit TSU in response to the touch sensing control signal. In addition, by receiving the sensing signals fed back from the driving electrodes TE and the touch sensing signal detected through the sensing electrodes RE, the touch position of the user's body part, such as the user's finger F, and touch coordinate data corresponding to a touch area SDP are generated. The main driving circuit 200 receives touch coordinate data from the touch driving circuit 400 in real time (SS22).

Alternatively, the main driving circuit 200 may detect the user's touch area through the light sensing pixels LSP according to a second reference condition among the preset reference conditions (SS21). In this case, in the main driving circuit 200, the display pixels SP or infrared emitting pixels ISP of the display area DA emit light of a preset standard luminance, and the light sensing pixels LSP supply preset predetermined data voltages to the data lines DL so that a light sensing signal is generated. Then, a scan control signal is supplied to the display scan driver 110 and the light sensing scan driver 120 so that the display scan driver 110 and the light sensing scan driver 120 sequentially output the display scan signal and the sensing scan signal.

The main driving circuit 200 uses and analyzes the light sensing signals received through the light sensing pixels LSP to generate touch coordinate data corresponding to the touch position of a body part such as the user's finger F and the touch areas SDP (SS22). In other words, in SS22, body part contact area is detected.

Figure 12:
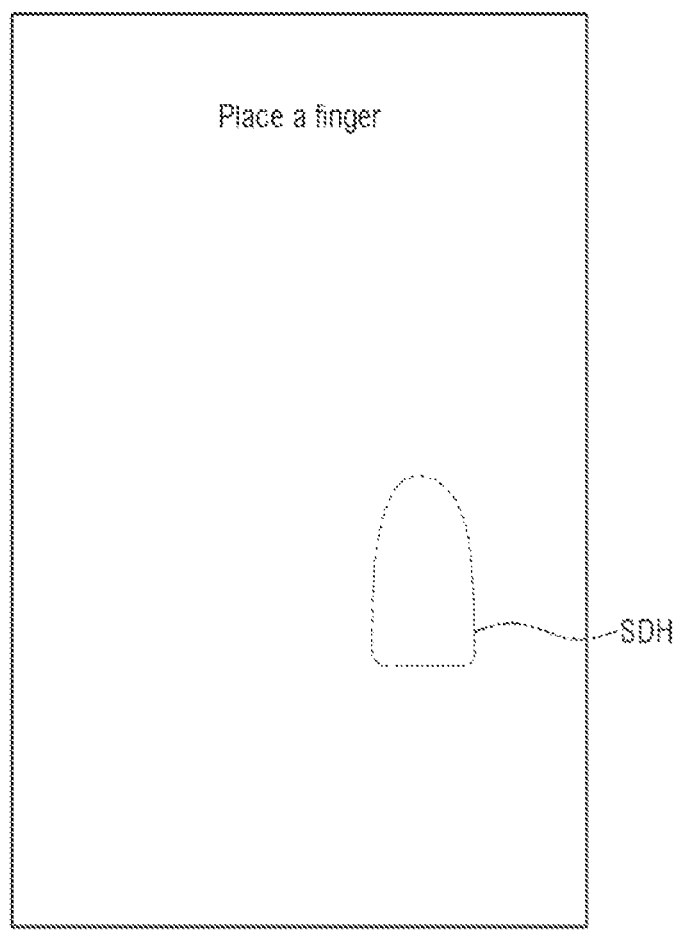
FIG. 12 is a diagram showing a process of analyzing the touch shape of a body part and the touch area.

FIG. 12 is a diagram showing a process of analyzing the touch shape of a body part and the touch area.

The main driving circuit 200 determines the touch position of the body part, the touch area, and the touch non-sensing areas, which exclude the touch area, in the display area DA through touch coordinate data generated or received according to the first reference condition, the second reference condition, or the third reference condition. Additionally, the main driving circuit 200 detects a touch shape along the outside or edge of the touch area by distinguishing boundary coordinates of the touch area and the touch non-sensing area. In addition, touch area information SDH including touch shape information and touch area information may be detected by calculating the area according to the pixel arrangement in the touch area (SS31). In other words, in SS31, the body part contact area and shape may be analyzed.

Figure 13:
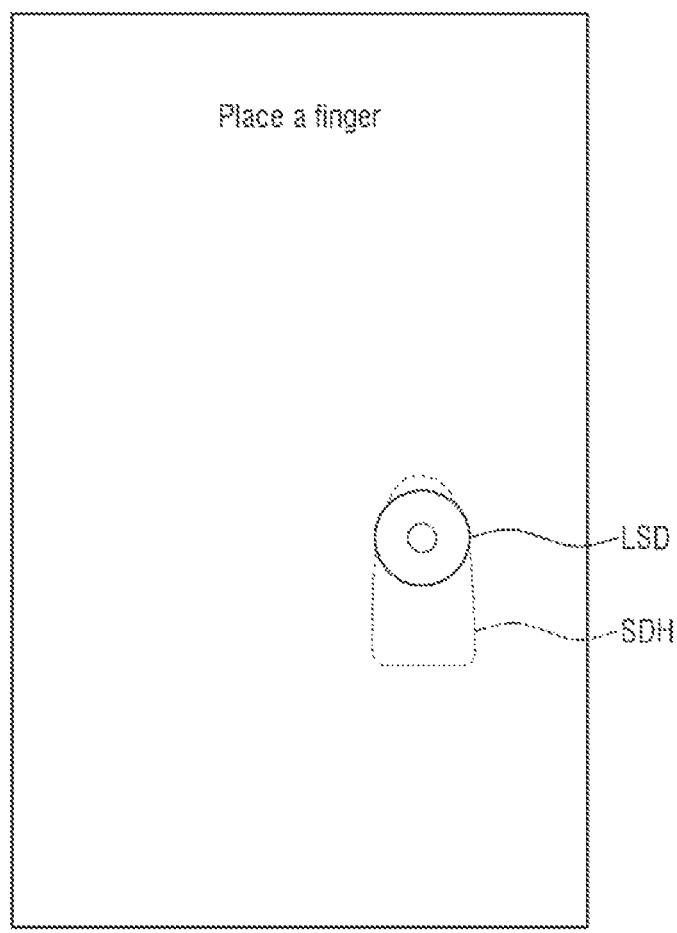
FIG. 13 is a diagram showing a process of setting a biometric information measurement area in a body part touch area.

FIG. 13 is a diagram showing a process of setting a biometric information measurement area in a body part touch area.

The main driving circuit 200 compares the touch shape information and the touch area information included in the touch area information SDH with the stored shape information and area information for each body part, so that the touched body part information in the display area DA is classified in real time. For example, the main driving circuit 200 may classify the touch body part information into a finger, a face, a scalp, and the like according to comparison results between the touch shape information and the touch area information included in the touch area information SDH.

The main driving circuit 200 determines and sets a biometric information measurement area LSD in the touch area according to the touch shape and touch area based on the classified body part information and the touch area information SDH. Here, the biometric information measurement area LSD may be set in any one of a polygonal shape such as a triangle, square, or pentagon or in any one shape among a circular, a semicircular, an elliptical, and a curved mottle shape according to the classified body part information.

Figure 14:
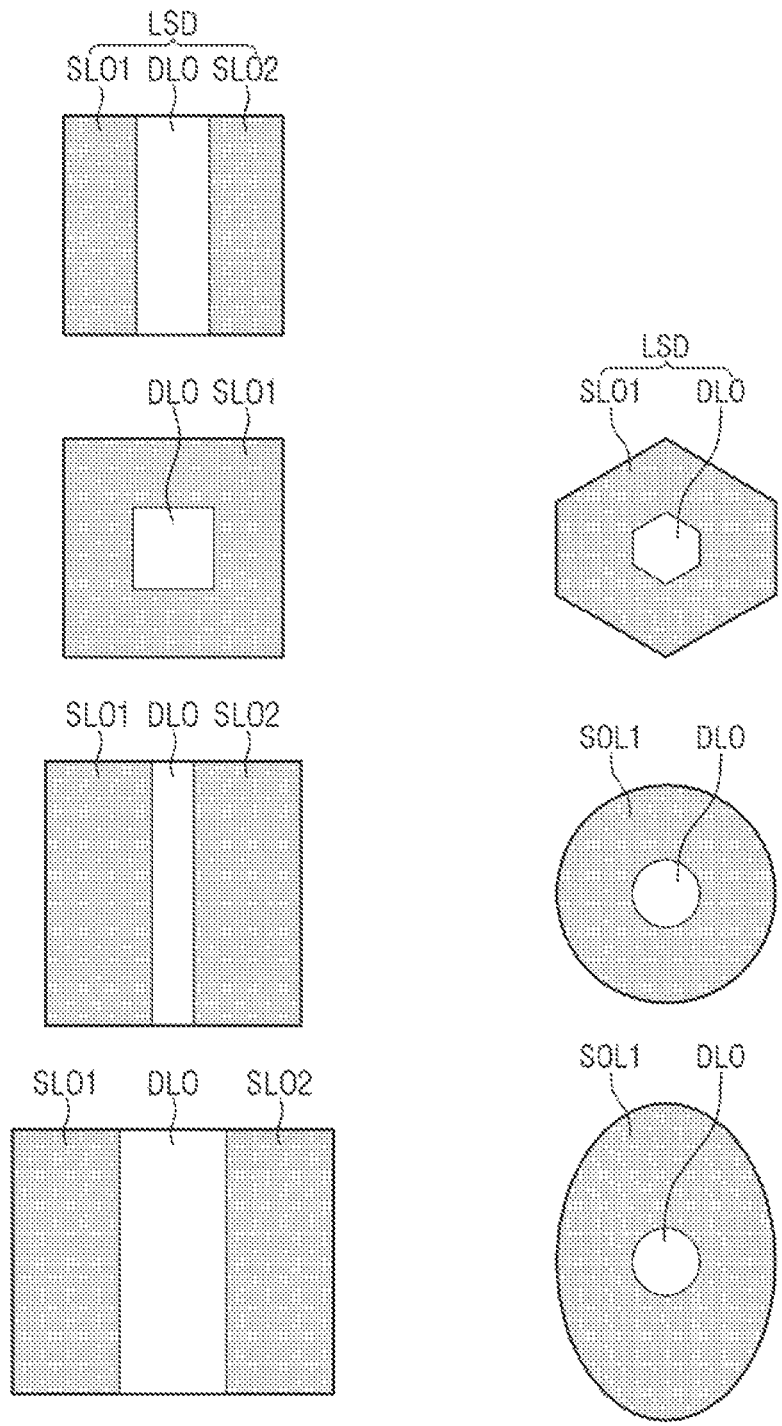
FIG. 14 is a diagram illustrating a process of setting an emission area and a light sensing area with respect to the biometric information measurement area.

FIG. 14 is a diagram illustrating a process of setting an emission area and a light sensing area with respect to the biometric information measurement area.

Referring to FIG. 14, the main driving circuit 200 determines the biometric information measurement area LSD according to the body part information, the touch shape, and the touch area, and divide the biometric information measurement area LSD into at least one emission area SLO1 or SLO2 and at least one light sensing area DLO (SS42).

For example, the main driving circuit 200 may set the biometric information measurement area LSD in any one of a polygonal shape such as a triangle, square, or pentagon or in any one shape among a circular shape, a semicircular shape, an elliptical shape, and a curved mottle shape. In this case, the biometric information measurement area LSD may be determined and set by classifying the arrangements in which at least one light sensing area DLO may be disposed adjacent to at least one emission area SLO1 or SLO2, at least one light sensing area DLO may be included in at least one emission area SLO1, or at least one light sensing area DLO may be disposed between the plurality of emission areas SLO1 and SLO2.

At least one emission area SLO1 or SLO2 may be set in any one of a polygonal shape, such as a triangle, rectangle, or pentagon, or in any one shape among a circular shape, a semicircular shape, an elliptical shape, and a curved mottle shape. In addition, at least one light sensing area DLO may also be set in in any one of a polygonal shape, such as a triangle, rectangle, or pentagon, or in any one shape among a circular shape, a semicircular shape, an elliptical shape, and a curved mottle shape.

Thereafter, the main driving circuit 200 selects the emission color of the display pixels SP included in at least one emission area SLO1 or SLO2 in the biometric information measurement area LSD as green, red or the like according to the body part information, the touch shape, and the touch area. Alternatively, the main driving circuit 200 may reduce or expand the infrared emission wavelength band of the infrared light emitting pixels ISP included in at least one emission area SLO1 or SLO2 in the biometric information measurement area LSD according to the body part information, the touch shape, and the touch area. The main driving circuit 200 may raise or lower the luminance value of the display pixels SP for each emission color included in at least one emission area SLO1 or SLO2 in the biometric information measurement area LSD according to the body part information, the touch shape, and the touch area (SS43).

The main driving circuit 200 compares the user's touch shape and the touch area on the display area DA with the biometric information measurement area LSD in real time. If the user's touch shape and the touch area on the display area DA and the biometric information measurement area LSD are changed, the biometric information measurement area LSD is re-detected (SS44).

However, if the user's touch shape and touch area on the display area DA and the biometric information measurement area LSD are maintained, setting information for the biometric information measurement area LSD is determined (SS45). Further, the main driving circuit 200 drives the display pixels SP or infrared light emitting pixels ISP included in at least one emission area SLO1 or SLO2 of the biometric information measurement area LSD, and measures the biometric information such as the user's blood pressure by receiving light sensing signals through light sensing pixels LSP included in the light sensing area DLO of the biometric information measurement area LSD.

Figure 15:
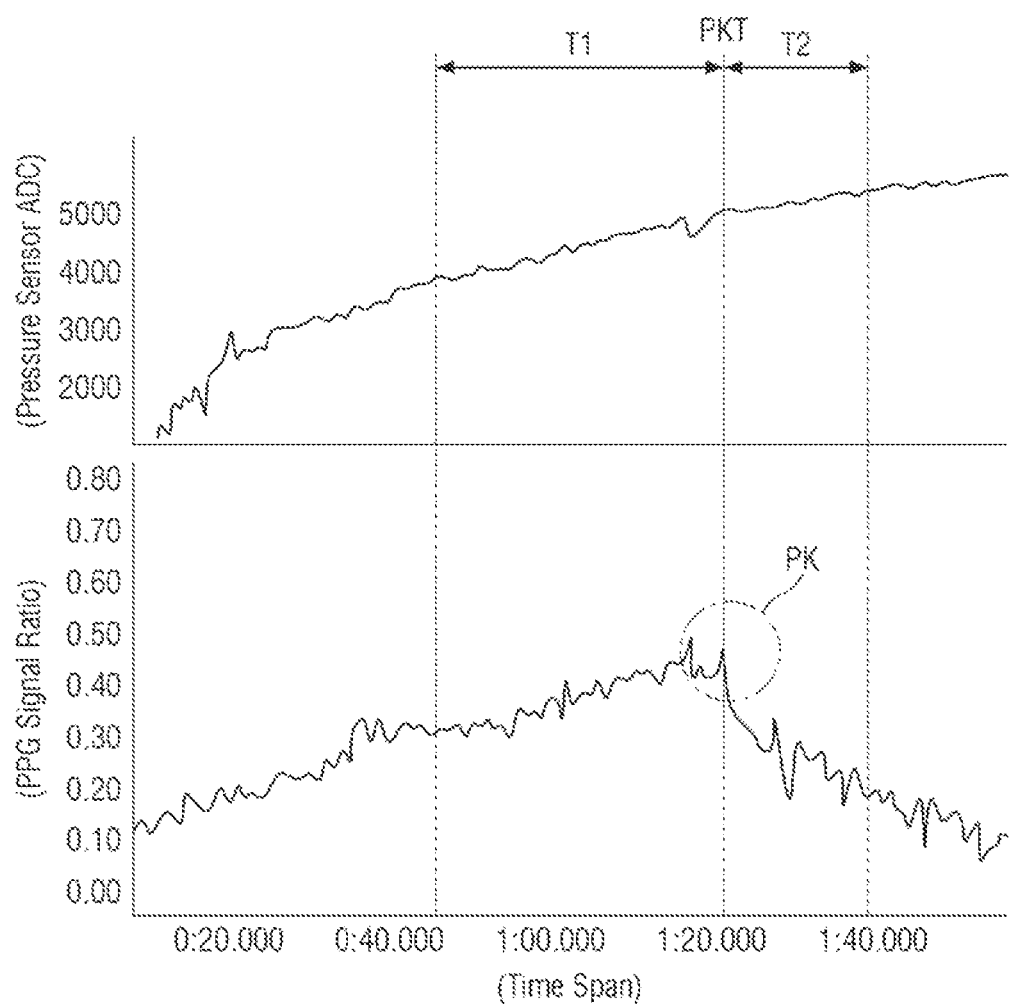
FIG. 15 is a graph for illustrating a method of calculating a blood pressure from the biometric information according to an embodiment of the present disclosure.

FIG. 15 is a graph for illustrating a method of calculating a blood pressure from the biometric information according to an embodiment of the present disclosure.

Referring to FIG. 15, during the systole of the heart, blood ejected from the left ventricle of the heart moves to peripheral tissues, thus increasing blood volume on the arterial side. In addition, during the systole of the heart, red blood cells carry more oxyhemoglobin to the peripheral tissues. During the diastole of the heart, there is partial suction of blood from the peripheral tissues toward the heart. When light is irradiated to the peripheral blood vessels, the irradiated light is absorbed by the peripheral tissues. Light absorbance is dependent on hematocrit and blood volume. The light absorbance may have a maximum value during the systole of the heart and a minimum value during the diastole of the heart. Accordingly, the amount of light sensed by the light sensing element PD may be the least during the systole of the heart and the most during the diastole of the heart.

Further, when the user puts a finger F on the display panel 100 and lifts it off in the blood pressure measurement mode, a force (e.g., contact force) applied to the force sensing unit PSU may gradually increase to reach a maximum value, and then may gradually decrease. When the contact force increases, blood vessels may become narrow, resulting in a decrease of or no blood flow. When the contact force decreases, the blood vessels expand, and thus blood flows again. A further decrease of the contact force results in greater blood flow. Therefore, the change in the amount of light sensed by the light sensing pixel LSP may be proportional to the change in blood flow. Accordingly, the main driving circuit 200 generates a pulse wave signal according to the pressure applied by the user, based on a digitally converted pressure data value (e.g., ADC of the pressure sensor) calculated by the pressure sensing unit PSU and an optical signal (e.g, PPG signal ratio) according to the amount of light sensed by the light sensing element PD. The pulse wave signal may have a waveform that vibrates according to a heartbeat cycle.

The main driving circuit 200 may estimate blood pressures of the blood vessels of the finger F based on time differences between time points PKT corresponding to peaks PK of the calculated pulse wave signal and time points corresponding to peaks of the filtered pulse wave.

For example, the main driving circuit 200 may calculate pulse wave signals during preset periods T1 and T2 before and after the time points PKT corresponding to the peaks PK of the calculated pulse wave signal, and may detect blood pressure according to differences between the pulse wave signals. Among the estimated blood pressure values, a maximum blood pressure value may be determined as a systolic blood pressure value, and a minimum blood pressure value may be determined as a diastolic blood pressure value. Further, additional blood pressure values such as an average blood pressure value or the like may be calculated using the estimated blood pressure values. The main driving circuit 200 displays the detected blood pressure information on the display area DA.

The method for measuring the blood pressure described above is only an example, various other methods are disclosed in Korean Patent Application Publication No. 10-2018-0076050, Korean Patent Application Publication No. 10-2017-0049280, and Korean Patent Application Publication No. 10-2019-0040527, the disclosures of which are incorporated by reference herein in their entireties.

Figure 16:
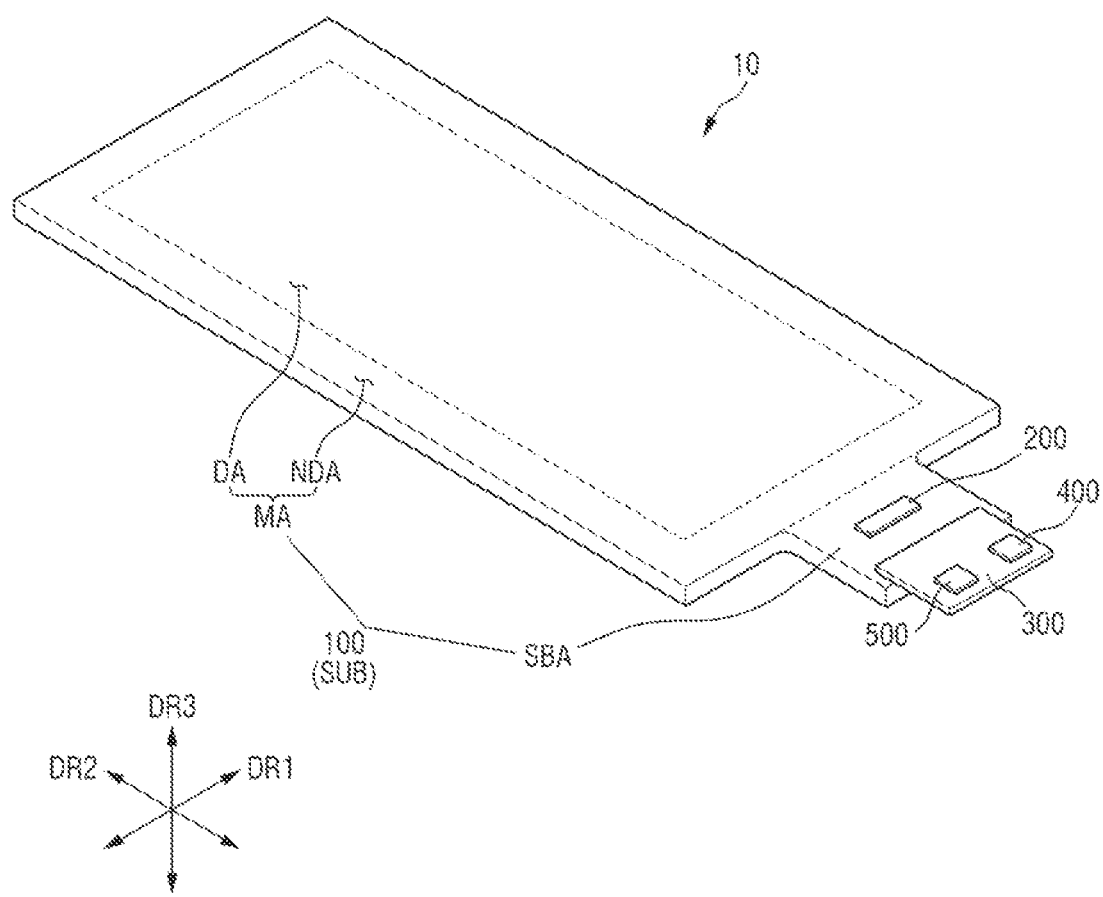
FIG. 16 is a perspective view illustrating a display device according to another embodiment of the present disclosure.

FIG. 16 is a perspective view illustrating a display device according to another embodiment of the present disclosure. Further, FIG. 17 is a side view showing the configuration of the display device shown in FIG. 16.

Figure 17:
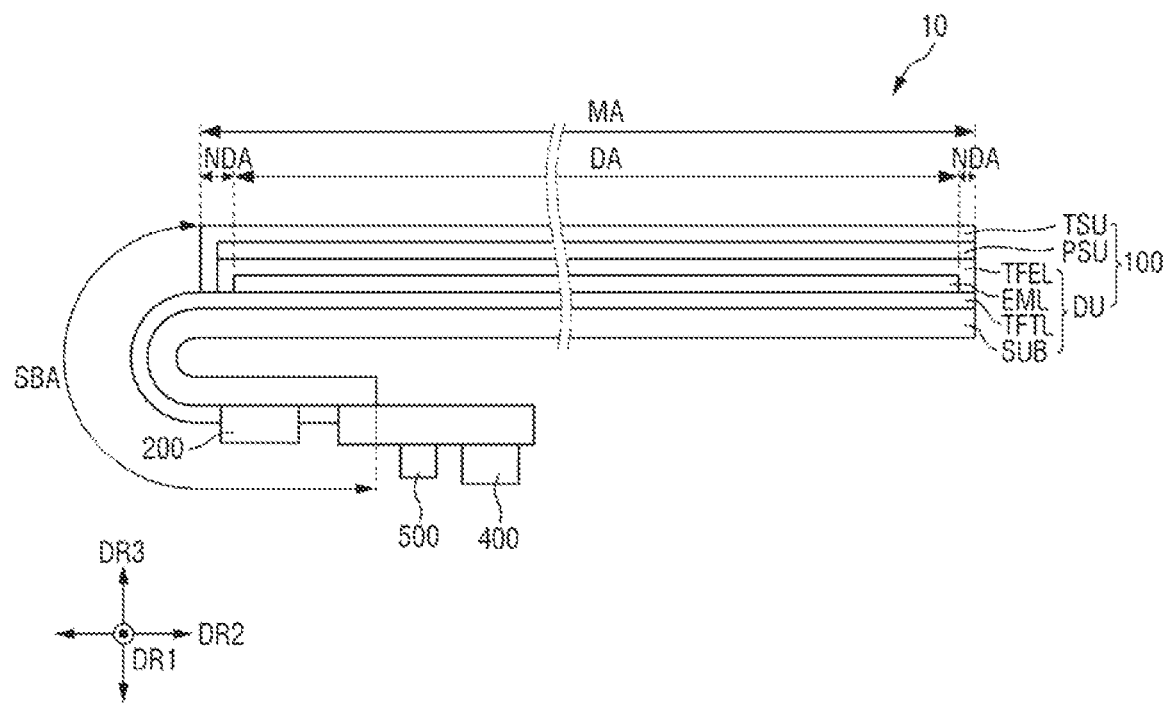
FIG. 17 is a side view showing the configuration of the display device shown in FIG. 16.

Referring to FIGS. 16 and 17, a blood pressure detection circuit 500 may be formed separately from the main driving circuit 200 and the touch driving circuit 400. The blood pressure detection circuit 500 may be formed of an integrated circuit (IC), and may be attached onto the display panel 100 or the circuit board 300 by a chip on glass (COG) method, a chip on plastic (COP) method, or an ultrasonic bonding method, but is not limited thereto. For example, the blood pressure detection circuit 500 may be attached onto the circuit board 300 by a chip on film (COF) method.

The blood pressure detection circuit 500 may select any one of preset reference conditions and generate a control signal according to the reference condition to detect the user's touch area during the period for measuring biometric information such as blood pressure. Accordingly, the blood pressure detection circuit 500 may transmit a touch sensing control signal to the main driving circuit 200 according to a second reference condition among preset reference conditions so that the main driving circuit 200 detects the user's touch area through light sensing pixels LSP.

The blood pressure detection circuit 500 analyzes the touch coordinate data received from the main driving circuit 200 to detect contact area information including the contact position, contact shape, and contact area of the user's body part. In addition, the biometric information measurement area may be set using the contact area information of the user's body part, and biometric information measurement conditions may be subdivided. Subsequently, the blood pressure detection circuit 500 may receive the light sensing signals received from the main driving circuit 200 to measure biometric information such as a user's blood pressure.

Figure 18:
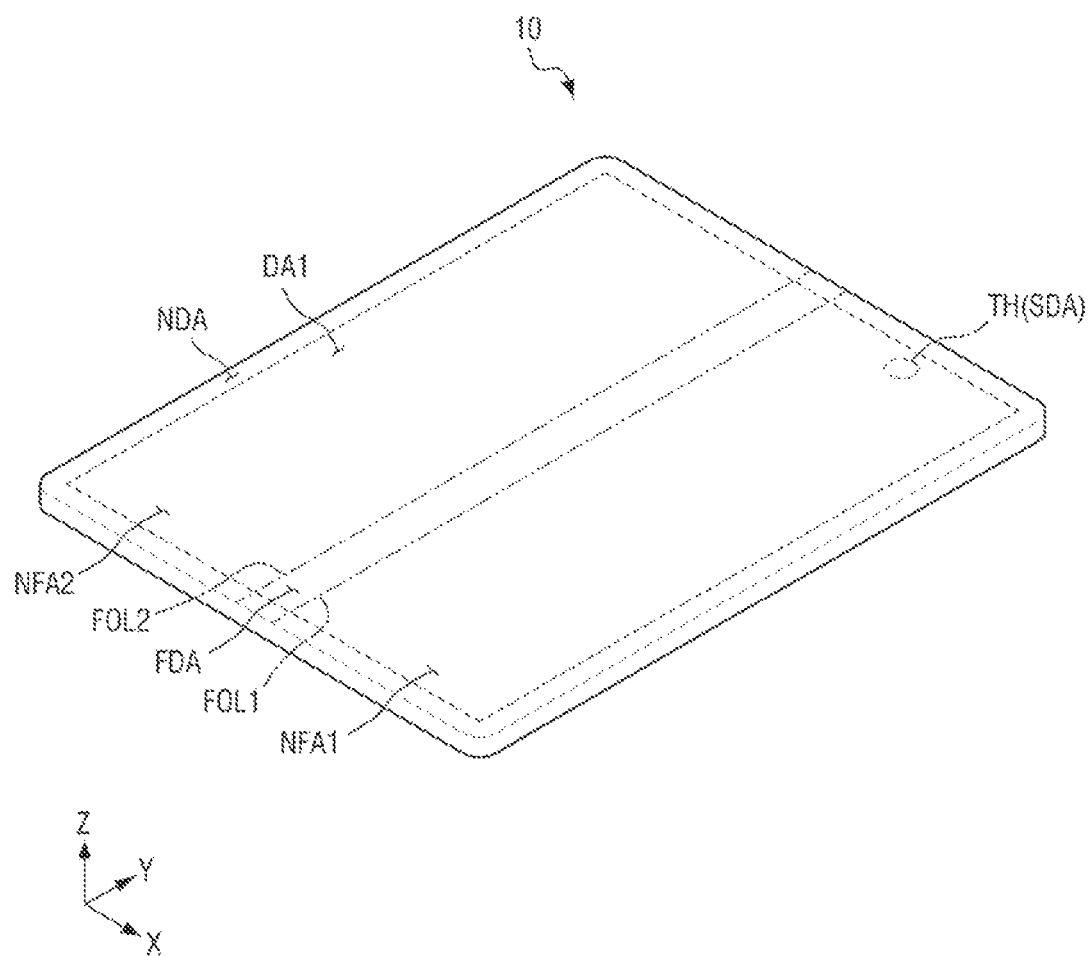
FIGS. 18 and 19 are perspective views illustrating display devices according to other embodiments of the present disclosure.
Figure 19:
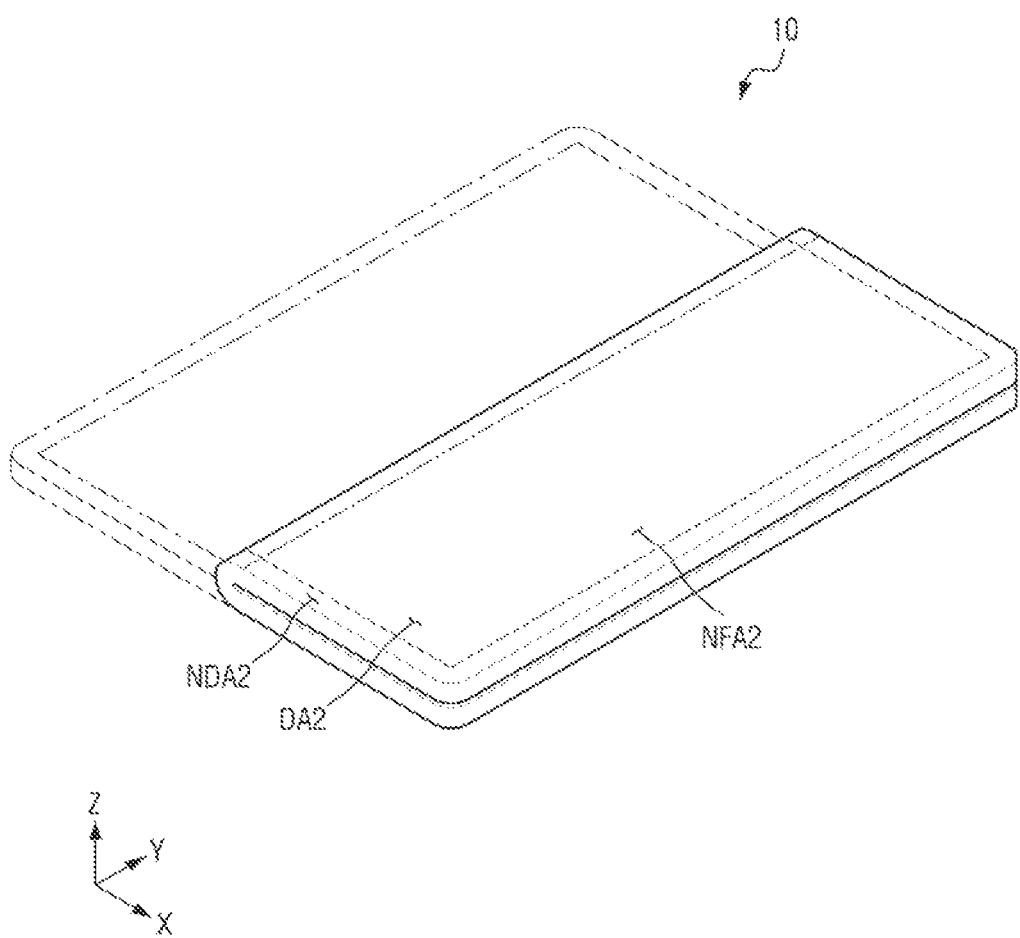

FIGS. 18 and 19 are perspective views illustrating display devices according to other embodiments of the present disclosure.

It has been illustrated in FIGS. 18 and 19 that a display device 10 is a foldable display device folded in an X-axis direction. The display device 10 may be maintained in both a folded state and an unfolded state. The display device 10 may be folded in an in-folding manner in which a front surface thereof is disposed inside. When the display device 10 is bent or folded in the in-folding manner, front surfaces of the display device 10 may be disposed to face each other. Alternatively, the display device 10 may be folded in an out-folding manner in which a front surface thereof is disposed outside. When the display device 10 is bent or folded in the out-folding manner, rear surfaces of the display device 10 may be disposed to face each other.

A first non-folding area NFA1 may be disposed on one side, for example, the right side of a folding area FDA. A second non-folding area NFA2 may be disposed on the other side, for example, on the left side of the folding area FDA. The touch sensing units TSU according to an embodiment of the present disclosure may be formed and disposed on the first non-folding area NFA1 and the second non-folding area NFA2, respectively.

A first folding line FOL1 and a second folding line FOL2 may extend in a Y-axis direction, and the display device 10 may be folded in the X-axis direction. Accordingly, a length of the display device 10 in the X-axis direction may be reduced by approximately half, and thus, a user may conveniently carry the display device 10.

An extension direction of the first folding line FOL1 and an extension direction of the second folding line FOL2 are not limited to the Y-axis direction. For example, the first folding line FOL1 and the second folding line FOL2 may extend in the X-axis direction, and the display device 10 may be folded in the Y-axis direction. In this case, a length of the display device 10 in the Y-axis direction may be reduced by approximately half. Alternatively, the first folding line FOL1 and the second folding line FOL2 may extend in a diagonal direction of the display device 10 corresponding to a direction between the X-axis direction and the Y-axis direction. In this case, the display device 10 may be folded in a triangular shape.

When the first folding line FOL1 and the second folding line FOL2 extend in the Y-axis direction, a length of the folding area FDA in the X-axis direction may be smaller than a length of the folding area FDA in the Y-axis direction. In addition, a length of the first non-folding area NFA1 in the X-axis direction may be greater than the length of the folding area FDA in the X-axis direction. A length of the second non-folding area NFA2 in the X-axis direction may be greater than the length of the folding area FDA in the X-axis direction.

A first display area DA1 may be disposed on a front surface of the display device 10. The first display area DA1 may overlap the folding area FDA, the first non-folding area NFA1, and the second non-folding area NFA2. Therefore, when the display device 10 is unfolded, an image may be displayed in a front surface direction in the folding area FDA, the first non-folding area NFA1, and the second non-folding area NFA2 of the display device 10.

A second display area DA2 may be disposed on a rear surface of the display device 10. The second display area DA2 may overlap the second non-folding area NFA2. Therefore, when the display device 10 is folded, an image may be displayed in a front surface direction in the second non-folding area NFA2 of the display device 10.

It has been illustrated in FIGS. 18 and 19 that a through hole TH in which a camera SDA or the like is formed is disposed in the first non-folding area NFA1, but the present disclosure is not limited thereto. The through hole TH or the camera SDA may be disposed in the second non-folding area NFA2 or the folding area FDA.

Figure 20:
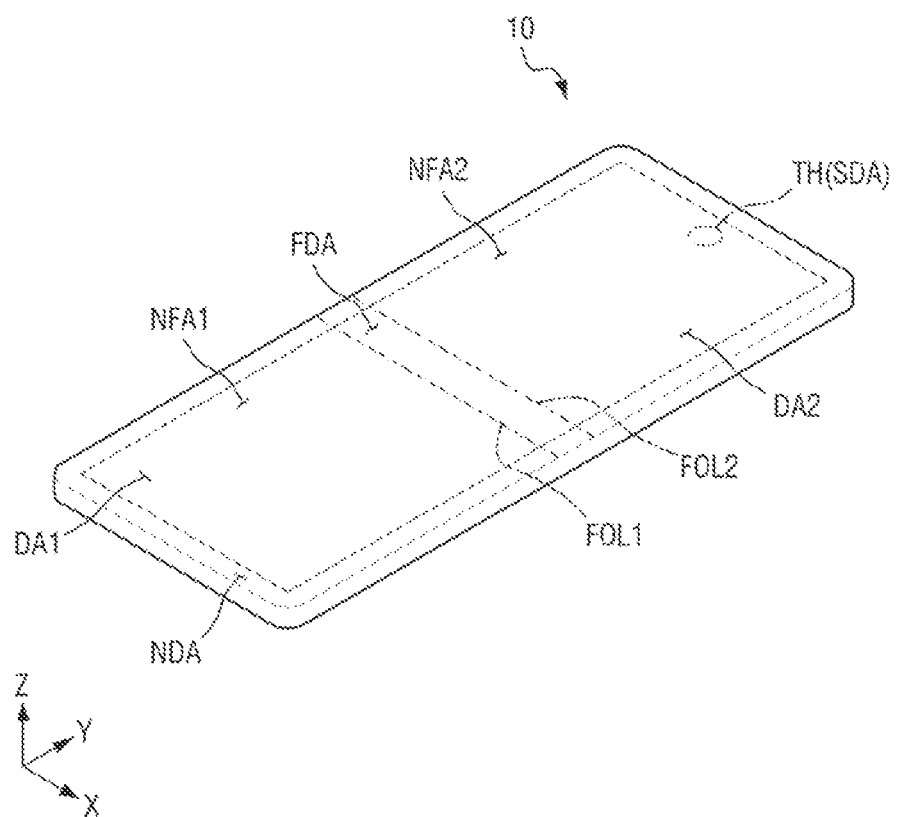
FIGS. 20 and 21 are perspective views illustrating display devices according to still other embodiments of the present disclosure.
Figure 21:
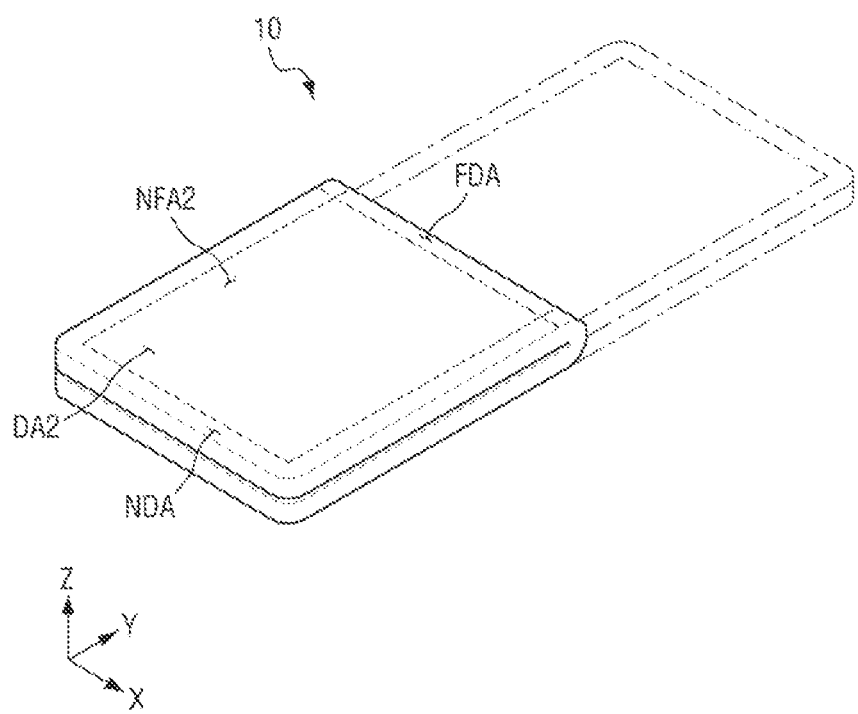

FIGS. 20 and 21 are perspective views illustrating display devices according to still other embodiments of the present disclosure.

It has been illustrated in FIGS. 20 and 21 that a display device 10 is a foldable display device folded in the Y-axis direction. The display device 10 may be maintained in both a folded state and an unfolded state. The display device 10 may be folded in an in-folding manner in which a front surface thereof is disposed inside. When the display device 10 is bent or folded in the in-folding manner, front surfaces of the display device 10 may be disposed to face each other. Alternatively, the display device 10 may be folded in an out-folding manner in which a front surface thereof is disposed outside. When the display device 10 is bent or folded in the out-folding manner, rear surfaces of the display device 10 may be disposed to face each other.

The display device 10 may include a folding area FDA, a first non-folding area NFA1, and a second non-folding area NFA2. The folding area FDA may be an area in which the display device 10 is folded, and the first non-folding area NFA1 and the second non-folding area NFA2 may be areas in which the display device 10 is not folded. The first non-folding area NFA1 may be disposed on one side, for example, the lower side of the folding area FDA. The second non-folding area NFA2 may be disposed on the other side, for example, on the upper side of the folding area FDA.

The touch sensing units TSU according to an embodiment of the present disclosure may be formed and disposed on the first non-folding area NFA1 and the second non-folding area NFA2, respectively.

On the other hand, the folding area FDA may be an area bent with a predetermined curvature in a first folding line FOL1 and a second folding line FOL2. Therefore, the first folding line FOL1 may be a boundary between the folding area FDA and the first non-folding area NFA1, and the second folding line FOL2 may be a boundary between the folding area FDA and the second non-folding area NFA2.

The first folding line FOL1 and the second folding line FOL2 may extend in the X-axis direction as illustrated in FIGS. 20 and 21, and the display device 10 may be folded in the Y-axis direction. Accordingly, a length of the display device 10 in the Y-axis direction may be reduced by approximately half, and thus, a user may conveniently carry the display device 10.

An extension direction of the first folding line FOL1 and an extension direction of the second folding line FOL2 are not limited to the X-axis direction. For example, the first folding line FOL1 and the second folding line FOL2 may extend in the Y-axis direction, and the display device 10 may be folded in the X-axis direction. In this case, a length of the display device 10 in the X-axis direction may be reduced by approximately half. Alternatively, the first folding line FOL1 and the second folding line FOL2 may extend in a diagonal direction of the display device 10 corresponding to a direction between the X-axis direction and the Y-axis direction. In this case, the display device 10 may be folded in a triangular shape.

When the first folding line FOL1 and the second folding line FOL2 extend in the X-axis direction as illustrated in FIGS. 20 and 21, a length of the folding area FDA in the Y-axis direction may be smaller than a length of the folding area FDA in the X-axis direction. In addition, a length of the first non-folding area NFA1 in the Y-axis direction may be greater than the length of the folding area FDA in the Y-axis direction. A length of the second non-folding area NFA2 in the Y-axis direction may be greater than the length of the folding area FDA in the Y-axis direction.

A first display area DA1 may be disposed on a front surface of the display device 10. The first display area DA1 may overlap the folding area FDA, the first non-folding area NFA1, and the second non-folding area NFA2. Therefore, when the display device 10 is unfolded, an image may be displayed in a front surface direction in the folding area FDA, the first non-folding area NFA1, and the second non-folding area NFA2 of the display device 10.

A second display area DA2 may be disposed on a rear surface of the display device 10. The second display area DA2 may overlap the second non-folding area NFA2. Therefore, when the display device 10 is folded, an image may be displayed in a front surface direction in the second non-folding area NFA2 of the display device 10.

It has been illustrated in FIGS. 20 and 21 that a through hole TH in which a camera SDA or the like is disposed is disposed in the second non-folding area NFA2, but the present disclosure is not limited thereto. The through hole TH may be disposed in the first non-folding area NFA1 or the folding area FDA.

In concluding the detailed description, those skilled in the art will appreciate that many variations and modifications can be made to the embodiments set forth herein without substantially departing from the scope of the present disclosure. Therefore, the disclosed embodiments of the disclosure are used in a generic and descriptive sense and not for purposes of limitation.

What is claimed is:

1. A display device comprising:
   display pixels arranged in a display area of a display panel;
   light sensing pixels arranged in the display area;
   a display scan driver configured to cause the display pixels to emit light;
   a light sensing scan driver configured to cause the light sensing pixels to sense light, and
   a main driving circuit configured to measure a user's biometric information by using light sensing signals provided from the light sensing pixels,
   wherein the main driving circuit senses the user's touch area when the user's biometric information is measured, and sets a biometric information measurement area and a measurement condition, which includes an emission color and an emission luminance, according to a shape of a sensed touch area and touch area information to measure the user's biometric information,
   wherein the main driving circuit selects a reference condition among preset reference conditions to sense the user's touch area when the biometric information is measured, and senses the user's touch area by using the light sensing signals according to the selected reference condition and generates touch coordinate data corresponding to the user's touch area, or controls a touch driving circuit to receive touch coordinate data corresponding to the user's touch area.

2. The display device of claim 1, further comprising:
   infrared light emitting pixels arranged in the display area;
   a pressure sensing unit disposed on any one surface of the display panel and configured to sense a pressure applied by the user's body part and output a pressure sensing signal;
   a touch sensing unit disposed on a front surface of the display panel and configured to sense the user's touch and output a touch sensing signal; and
   the touch driving circuit configured to generate pressure data and pressure sensing coordinate data according to a magnitude change and an output position of the pressure sensing signal, and generate touch data and touch coordinate data according to a magnitude change and an output position of the touch sensing signal.

3. The display device of claim 2,
   wherein red, green, and blue display pixels among the display pixels of the display area and at least one of the light sensing pixels respectively form a first unit pixel,
   display pixels of the display area and at least one of the infrared light emitting pixels respectively form a second unit pixel, and
   wherein the first and second unit pixels are alternately arranged in horizontal or vertical stripe form along a first and second directions of the display panel or are alternately arranged in zigzag pattern.

4. The display device of claim 2,
   wherein the main driving circuit transmits a touch sensing control signal to the touch driving circuit according to a first reference condition among the preset reference conditions,
   wherein the touch driving circuit supplies a touch driving signal to driving electrodes of the touch sensing unit in response to the touch sensing control signal, and wherein sensing signals fed back from the driving electrodes and touch sensing signals sensed from the sensing electrodes of the touch sensing unit are received by the touch driving circuit to generate and transmit the touch coordinate data corresponding to the user's touch area.

5. The display device of claim 2,
wherein the main driving circuit transmits a scan control signal to the display scan driver and the light sensing scan driver according to a second reference condition among the preset reference conditions, supplies data voltages of a preset voltage magnitude to data lines of the display area to drive the display pixels and the light sensing pixels, and
wherein the light sensing signals are received through the light sensing pixels to sense the user's touch area and generate touch coordinate data corresponding to the user's touch area.

6. The display device of claim 2,
wherein the main driving circuit analyzes the touch coordinate data generated according to at least any one reference condition among the preset reference conditions to detect a touch area information including a touch position, a touch shape, and a touch area of the user's body part, compares the touch area information to a preset database to set the biometric information measurement area, and determine and set the biometric information measurement conditions including an emission color and an emission luminance with respect to the biometric information measurement area by subdividing to measure the user's biometric information.

7. The display device of claim 6,
wherein the main driving circuit compares touch shape information and touch area information included in the touch area information to stored shape information and area information for body parts of the user in real time to identify the touched body part information in the display area, and determines and sets the biometric information measurement area in the user's touch area according to a touch shape and a touch area based on the identified touch body part information and the touch area information.

8. The display device of claim 7,
wherein the main driving circuit sets the biometric information measurement area as any one of a polygonal shape among a triangle, a square, a pentagon, and a hexagon or as any one shape among a circular shape, a semicircular shape, an elliptical shape, and a curved mottle shape.

9. The display device of claim 7,
wherein the main driving circuit divides the biometric information measurement area into at least one emission area and at least one light sensing area according to the body part information, the touch shape and the touch area,
wherein the biometric information measurement area is determined and set so that the at least one light sensing area is disposed adjacent to the at least one emission area, so that the at least one light sensing area is included in the at least one emission area, and so that the at least one light sensing area is disposed between the plurality of emission areas.

10. The display device of claim 9,
wherein the at least one emission area is set to be any one of a polygonal shape among a triangle, a square, a pentagon, and a hexagon, or as any one shape among a circular shape, a semicircular shape, an elliptical shape, and a curved mottle shape, and
wherein the at least one light sensing area is set to be any one of a polygonal shape among a triangle, a square, a pentagon, and a hexagon, or as any one shape among a circular shape, a semicircular shape, an elliptical shape, and a curved mottle shape.

11. The display device of claim 9,
wherein the main driving circuit selects an emission color of the display pixels included in at least one emission area in the biometric information measurement area as green, red, or blue according to the user's body part information, the touch shape, and the touch area, changes an infrared emission wavelength band of infrared light emitting pixels included in the at least one emission area, and changes a luminance value for each emission color of the display pixels included in the at least one emission area.

12. A display device comprising:
display pixels arranged in a display area of a display panel;
light sensing pixels arranged in the display area;
infrared light emitting pixels arranged in the display area;
a display scan driver driven so that the display pixels emit light;
a light sensing scan driver driven so that the light sensing pixels sense light;
a touch sensing unit disposed on a front surface of the display panel and configured to sense a user's touch and output a touch sensing signal;
a touch driving circuit configured to generate touch data and touch coordinate data according to a magnitude change and an output position of the touch sensing signal; and
a main driving circuit configured to measure the user's biometric information by using light sensing signals received through the light sensing pixels,
wherein the main driving circuit senses the user's touch area when the biometric information is measured, and sets a biometric information measurement area and a measurement condition that includes an emission color and an emission luminance according to a shape of a sensed touch area and touch area information to measure the user's biometric information,
wherein the main driving circuit selects any one reference condition among preset reference conditions to sense the user's touch area when the biometric information is measured, and senses the user's touch area by using the light sensing signals according to the selected reference condition and generates touch coordinate data corresponding to the touch area, or controls the touch driving circuit to receive touch coordinate data corresponding to the user's touch area.

13. The display device of claim 12, further comprising a pressure sensing unit disposed on any one surface of the display panel and configured to sense a pressure applied by the user's body part and output a pressure sensing signal,
wherein the touch driving circuit generates a pressure data and pressure sensing coordinate data according to a magnitude change and an output position of the pressure sensing signal and generates a touch data and touch coordinate data according to a magnitude change and an output position of the touch sensing signal.

14. The display device of claim 13,
wherein the main driving circuit analyzes the touch coordinate data generated according to at least any one reference condition among the preset reference conditions to detect a touch area information including a touch position, a touch shape, and a touch area of the user's body part, compares the touch area information to a preset database to set the biometric information measurement area, and determine biometric information measurement conditions including an emission color and an emission luminance in respect to the biometric information measurement area by subdividing to measure the user's biometric information.

15. The display device of claim 14,
wherein the main driving circuit compares touch shape information and touch area information included in the touch area information to stored shape information and area information for body parts of the user in real time to identify the touched body part information in the display area, and determines the biometric information measurement area in the user's touch area according to a touch shape and a touch area based on identified body part information and the touch area information.

16. The display device of claim 15,
wherein the main driving circuit divides the biometric information measurement area into at least one emission area and at least one light sensing area according to the body part information, the touch shape and the touch area,
wherein the biometric information measurement area is set so that the at least one light sensing area is disposed adjacent to the at least one emission area, so that the at least one light sensing area is included in the at least one emission area, and so that the at least one light sensing area is disposed between the plurality of emission areas.

17. The display device of claim 16,
wherein the at least one emission area is set to be any one of a polygonal shape among a triangle, a square, a pentagon, and a hexagon, or as any one shape among a circular shape, a semicircular shape, an elliptical shape, and a curved mottle shape, and
wherein the at least one light sensing area is set to be any one of a polygonal shape among a triangle, a square, a pentagon, and a hexagon, or as any one shape among a circular shape, a semicircular shape, an elliptical shape, and a curved mottle shape.

18. The display device of claim 16,
wherein the main driving circuit selects an emission color of the display pixels included in at least one emission area in the biometric information measurement area as green, red, or blue according to the user's body part information, the touch shape, and the touch area, changes an infrared emission wavelength band of infrared light emitting pixels included in the at least one emission area, and changes a luminance value for each emission color of the display pixels included in the at least one emission area.

* * * * *